US012521507B2

(12) United States Patent
Kim

(10) Patent No.: US 12,521,507 B2
(45) Date of Patent: Jan. 13, 2026

(54) SYSTEM AND METHOD FOR AN ENDOSCOPIC AIRWAY DEVICE

(71) Applicant: Kevin Chong Kim, Holmdel, NJ (US)

(72) Inventor: Kevin Chong Kim, Holmdel, NJ (US)

( * ) Notice: Subject to any disclaimer, the term of this patent is extended or adjusted under 35 U.S.C. 154(b) by 160 days.

(21) Appl. No.: 17/991,827

(22) Filed: Nov. 21, 2022

(65) Prior Publication Data

US 2023/0084801 A1 Mar. 16, 2023

Related U.S. Application Data

(63) Continuation-in-part of application No. 17/752,758, filed on May 24, 2022, now Pat. No. 12,453,829, (Continued)

(51) Int. Cl.
*A61M 16/04* (2006.01)
*A61B 1/00* (2006.01)
(Continued)

(52) U.S. Cl.
CPC ..... *A61M 16/0463* (2013.01); *A61B 1/00135* (2013.01); *A61B 1/2736* (2013.01); (Continued)

(58) Field of Classification Search
CPC .......... A61M 16/0463; A61M 16/0436; A61M 16/1005; A61M 16/0488; (Continued)

(56) References Cited

U.S. PATENT DOCUMENTS 5,241,956 A * 9/1993 Brain ................ A61M 16/0415 128/207.14
7,089,942 B1 8/2006 Grey
(Continued)

FOREIGN PATENT DOCUMENTS

WO WO-2005046751 A2 * 5/2005 ........ A61M 16/0486

OTHER PUBLICATIONS

Effect of a Novel Anatomically Shaped Endotracheal Tube on Intubation-Related Injury Arie Gordin, MD; Neil K. Chadha, MBChB(Hons), FRCS(ORL-HNS); Paolo Campisi, MSc, MD, FRCSC; Igor Luginbuehl, MD; Glenn Taylor, MD; Vito Forte, MD (Year: 2010).*

(Continued)

*Primary Examiner* — Michael J Carey
*Assistant Examiner* — Megan Elizabeth Monahan
(74) *Attorney, Agent, or Firm* — Jessica W. Smith; LOZA & LOZA, LLP

(57) ABSTRACT

An airway device includes an outertube and a scope channel partially enclosed by the outertube. An intraluminal space in the outertube, not occupied by the scope channel, provides a passageway for air flow to the patient. An esophageal cuff is disposed distally on the scope channel. When inflated, the esophageal cuff secures the airway device in the proximal esophagus of the patient and helps to prevent gastric reflux by mechanically blocking gastric content from entering into the larynx. An inflatable bladder is attached at an anterior surface of the scope channel between the esophageal cuff and a distal opening of the outertube. When inflated, the bladder forms a tubular ring that pushes against the epiglottis and/or other soft tissue towards a wall of the hypopharynx to produce an unhindered air passage into the patient's trachea.

15 Claims, 13 Drawing Sheets

Related U.S. Application Data which is a continuation-in-part of application No. 17/110,268, filed on Dec. 2, 2020, now Pat. No. 11,793,962.

(51) Int. Cl.
*A61B 1/273* (2006.01)
*A61M 16/10* (2006.01)

(52) U.S. Cl.
CPC .... *A61M 16/0436* (2014.02); *A61M 16/0488* (2013.01); *A61M 16/1005* (2014.02); *A61M 2205/3344* (2013.01)

(58) Field of Classification Search
CPC ....... A61M 2205/3344; A61B 1/00135; A61B 1/2736; A61B 2018/00488; A61L 27/3679; A61L 27/3882; A61L 2430/22; A61N 2005/0609
See application file for complete search history.

(56) References Cited

U.S. PATENT DOCUMENTS

| | | | | |
|---|---|---|---|---|
| 11,202,561 | B2 * | 12/2021 | Molnar | A61M 16/0456 |
| 11,602,605 | B1 | 3/2023 | Kim | |
| 11,744,972 | B1 | 9/2023 | Kim | |
| 2004/0020491 | A1 * | 2/2004 | Fortuna | A61M 16/0486 128/200.26 |
| 2010/0249639 | A1 * | 9/2010 | Bhatt | A61B 1/00135 128/207.14 |
| 2019/0083732 | A1 * | 3/2019 | Vadivelu | A61M 16/0463 |
| 2020/0345214 | A1 * | 11/2020 | Poulsen | A61B 1/00103 |
| 2022/0047152 | A1 * | 2/2022 | Bob | A61B 1/018 |

OTHER PUBLICATIONS

PCT/US2023/036888, International search report and Written Opinion mailed on Feb. 12, 2024.

* cited by examiner

H-H (4 : 1)

SYSTEM AND METHOD FOR AN ENDOSCOPIC AIRWAY DEVICE

CROSS REFERENCE TO RELATED APPLICATIONS

This application is a continuation-in-part application under 35 U.S.C. § 120 of currently pending application Ser. No. 17/752,758, filed May 4, 2022, which is incorporated by reference in its entirety herein, which claims priority as a continuation-in-part application under 35 U.S.C. § 120 of currently pending U.S. patent application Ser. No. 17/110,268, filed Dec. 2, 2021, which is incorporated by reference in its entirety herein.

FIELD

This application relates to system and methods for an airway device, more particularly to an airway device configured for upper gastrointestinal endoscopy or upper gastrointestinal endoscopic procedures.

BACKGROUND

It is estimated that 31 million upper gastrointestinal (UGI) endoscopies and UGI endoscopic procedures (hereafter "gastroscopy" or "gastroscopies") are performed in the U.S. each year. A UGI endoscopy is performed to examine the esophagus, the stomach, and the first part of the small intestine (called the duodenum). UGI endoscopic procedures include endoscopic retrograde cholangiopancreatography (ERCP), endoscopic band ligation, percutaneous endoscopic gastromy (PEG), and transesophageal echocardiography (TEE). These procedures pose unique airway challenges with profound clinical ramifications for several reasons.

First, a gastroscope with a diameter of 8-13 mm, when inserted, takes up a significant portion of the patient's airway space. The result is the reduced total space available for the patient to breathe. This airway encroachment by the endoscope puts the patient at a high risk of airway compromise. In fact, one of the most common complications associated with gastroscopies is hypoxemia, and the reduction in the available airway space by the endoscope with its large cross-section area is a major contributing factor. According to the American Association of Nurse Anesthetists (AANA) Foundation closed claims database, respiratory events are the greatest cause of adverse outcomes. The American Society of Anesthesiologists (ASA) closed claims database reported that the most common sedation malpractice claim is inadequate oxygenation/ventilation, with more than 80% of claims of this nature resulting in brain damage or death.

Second, the presence of a gastroscope in the throat limits access to the airway by the anesthesiologist, when and if necessary. During gastroscopy, should a patient encounter clinically significant oxygen desaturation and respiratory insufficiency, the anesthesiologist has only minutes to correct the respiratory status before the patient sustains permanent damage to the brain and other organs of the body. Having to deal with the endoscope makes it more difficult for an anesthesiologist to rapidly restore the desperately needed respiratory stability.

Third, gastroscopies are mostly performed under deep sedation to minimize the patient's discomfort and suppress the gag, cough, and laryngospasm reflexes. Owing to these benefits, the popularity of deep sedation is increasing. This mode of anesthesia, nevertheless, entails very real risks. One consequence of deep sedation is the loss of pharyngeal and laryngeal muscle tone and suppression of respiratory drive, which causes upper airway obstruction and apnea, respectively. Both of these effects of deep sedation can lead to hypoxia or brain and other organ injuries. The general increasing trend of comorbidities, such as increasing age, sleep apnea, and obesity, in the US population can further exacerbate airway obstruction.

Fourth, the attenuation of protective airway reflexes and reduction of the tone of the upper and lower esophageal sphincters, the patient's supine position during gastroscopy, insufflation of air or fluid, and the irritation of the throat during a gastroscopy may contribute to regurgitation and aspiration of gastric contents. Aspiration can cause mild symptoms such as coughing, which can lead to premature termination of the procedure. Aspiration, often, however, cause more troubling problems such as laryngospasm, bronchospasm, and pneumonia, all of which can be potentially fatal.

Fifth, during gastroscopy, the airway is completely unprotected. There is no barrier to gastric refluxate, irrigating fluid, or the patient's secretions leaking into the airway. The situation is made worse due to the patient having reduced ability to clear such fluids and secretions once they enter the airway.

Presently existing oral and nasal airway devices are inadequate to effectively address the aforementioned difficulties associated with gastroscopies. Therefore, there is an urgent need for an airway device that can efficiently and effectively alleviate pharyngeal redundant tissue obstruction, and that can maintain a patent airway. There is also an urgent need for an airway device that is capable of interfacing with an oxygen delivery apparatus and a ventilator. There is, furthermore, a need for an airway device that permits separation of the digestive tract from the airway to prevent the gastric content from entering the airway. And, above all, there is an urgent need that the airway device is facile to introduce into the patient's throat since the ease and speed of establishing upper airway patency is a major determinant of patient outcome. Such a device will contribute to better patient outcomes and patient satisfaction. Additionally, it will help reduce the risk of litigation for providers and hospital systems, as inadequate ventilation and oxygenation are significant sources of malpractice lawsuits.

SUMMARY

In one aspect, a medical device includes a scope channel configured for insertion into a throat of a patient and an inflatable bladder attached to an anterior surface of a distal portion of the scope channel, wherein, in an inflated state, the bladder forms a ring that extends outwardly from the anterior surface of the scope channel.

In another aspect, a method of an airway device includes inserting a gastroscope through a scope channel; introducing the gastroscope into a patient and advancing the gastroscope into a proximal esophagus of the patient; and inserting the airway device into a throat and proximal esophagus of the patient until a tip of the scope channel is visible to the gastroscope. The method also includes pushing soft tissue and/or an epiglottis in a hypopharynx of the patient toward a peripheral wall of the hypopharynx using an inflatable bladder on the scope channel.

In another aspect, a medical device includes a scope channel configured for insertion into a throat of a patient and an outertube that encircles a portion of the scope channel and forms an intraluminal space between an interior wall of the outertube and an exterior wall of the scope channel. The medical device further includes an inflatable bladder attached to an anterior surface of a distal portion of the scope channel, wherein, in an inflated state, the bladder forms a ring that extends outwardly from the anterior surface of the scope channel and an inflatable cuff attached distally from the bladder on the scope channel, wherein the scope channel is positioned within an inner hole formed by the inflatable cuff, and wherein when inflated, the inflatable cuff expands radially from the scope channel.

In one or more of the above aspects, the inflatable bladder includes a posterior portion attached to the anterior surface of the distal portion of the scope channel, and an anterior portion, wherein, when the inflatable bladder is in an inflated state, the anterior portion extends outwardly at a proximate angle from the anterior surface of the scope channel.

In one or more of the above aspects, the anterior portion of the inflatable bladder, when the inflatable bladder is in an inflated state, is configured to retract soft tissue and/or epiglottis from a center to a periphery of a hypopharynx in the throat of the patient.

In one or more of the above aspects, the scope channel further comprises a bladder base. The bladder base includes a posterior surface coupled to the anterior surface of the distal portion of the scope channel and an anterior surface coupled to the posterior portion of the inflatable bladder.

In one or more of the above aspects, the bladder base further includes an indentation that spans an anterior surface of the bladder base configured to hold the anterior portion of the inflated bladder along a transverse axis of the bladder base. The bladder base also includes a cover attached by a spring hinge to a distal portion of the bladder base, wherein the cover, in a closed position, extends through an inner hole of the inflated bladder and covers a top portion of the indentation.

In one or more of the above aspects, the indentation of the bladder base is configured to hold the anterior portion and the posterior portion of the bladder in a deflated state, and wherein the hinged cover is configured to cover the indentation including the bladder in the deflated state.

In one or more of the above aspects, an inflatable cuff is attached distally from the bladder on the scope channel, wherein the scope channel is positioned within an inner hole formed by the inflatable cuff, and wherein when inflated, the inflatable cuff expands radially from the scope channel.

In one or more of the above aspects, the inflatable cuff is configured when inflated, to create a seal with a wall of a proximal esophagus.

In one or more of the above aspects, the first inflation lumen is coupled to the inflatable bladder, and the second inflation lumen is coupled to the inflatable cuff.

In one or more of the above aspects, the pressure regulator is configured to adjust a first pressure in the inflatable bladder using the first inflation lumen and adjust a second pressure in the inflatable cuff using the second inflation lumen.

In one or more of the above aspects, the outertube forms an interior space that houses at least a portion of the scope channel proximal to the inflatable bladder and distal from a proximal opening of the scope channel, wherein an interior wall of the outertube and an exterior wall of the scope channel form an intraluminal space.

In one or more of the above aspects, an adapter includes a first proximal mouth that forms a seal around a proximal opening of the scope channel and a distal mouth that forms a seal around the outertube. The adapter further includes a second proximal mouth and a sealed air flow passageway that extends from the second proximal mouth to the intraluminal space.

In one or more of the above aspects, a method includes creating a seal between the scope channel and a wall of the proximal esophagus using the airway device.

In one or more of the above aspects, a method includes inserting a gastroscope through the scope channel, introducing the gastroscope into the patient and advancing the gastroscope into the proximal esophagus of the patient; and inserting the airway device into a throat of the patient until a tip of the scope channel is visible to the gastroscope.

In one or more of the above aspects, a method includes inflating a cuff attached on a distal portion of the scope channel, wherein when inflated, the inflatable cuff expands radially from the scope channel and forms a seal between the scope channel and a wall of the proximal esophagus.

In one or more of the above aspects, a method includes inflating a bladder attached to an anterior surface of a distal portion of the scope channel, wherein, in an inflated state, the bladder forms a ring that extends outwardly from the anterior surface of the scope channel and pushes the soft tissue and/or the epiglottis in the hypopharynx of the patient toward the peripheral wall of the hypopharynx.

In one or more of the above aspects, a method includes adjusting a first pressure in the bladder using a first inflation lumen and adjusting a second pressure in the cuff using a second inflation lumen.

In one or more of the above aspects, a method includes inserting oxygenated air into a sealed air flow passageway that extends to an intraluminal space between an interior wall of an outertube and an exterior wall of the scope channel.

In one or more of the above aspects, a bladder base includes a posterior surface coupled to the anterior surface of the distal portion of the scope channel; an anterior surface coupled to the posterior portion of the inflatable bladder; and an indentation on the anterior surface of the bladder base, wherein the inflatable bladder, in a deflated state, folds into the indentation. The bladder case may also include a cover attached by a spring hinge to a distal portion of the anterior surface of the bladder base, wherein the cover extends along a top portion of the indentation and covers the inflatable bladder in the deflated state that is folded into the indentation.

In one or more of the above aspects, an inflatable bladder, during inflation, exerts a force on a proximal portion of the cover of the bladder base to open the cover, and wherein when the inflatable bladder is inflated, the cover by a recoil action of the spring hinge, returns to a closed position through an inner hole of the inflatable bladder and covers a top portion of the indentation.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Disclosed herein are a system, method, and device utilized to maintain a reliable, secure airway during the performance of a medical procedure involving an esophageal tube, such as a gastroscopic procedure, under sedation. An endoscopic airway device includes an outertube having a proximal end and a distal end. Disposed within the outertube and affixed to an internal wall of the outertube is a scope channel. The scope channel is a flexible tubular structure configured to permit the passage of a gastroscope. The extra space in the outertube, i.e., the intraluminal space not occupied by the scope channel, provides a passageway for air flow to the patient.

A distal end of the scope channel extends outwardly from a distal opening of the outertube. Disposed at the distal end of the scope channel is an inflatable esophageal cuff. When inflated, the esophageal cuff secures retention of the airway device in the hypopharynx/proximal esophagus of the patient and helps to prevent gastric reflux by mechanically blocking the gastric content from regurgitating into the pharynx and larynx. An inflatable bladder is attached at an anterior surface of the scope channel between the esophageal cuff and the distal opening of the outertube. When inflated, the bladder forms a circular or ellipsoidal ring forming an inner hole in the middle. The inflated bladder pushes against the soft tissue and the epiglottis in the hypopharynx from a center towards the peripheral wall of the hypopharynx, the region between the oropharynx at the level of the hyoid bone and the esophagus at the lower end of the cricoid cartilage. The space created in the middle of the inflated bladder provides an unhindered air passage into the patient's trachea. The bladder thus effectively clears the hypopharynx adjacent to the laryngeal opening to provide a clear airway.

Figure 1:
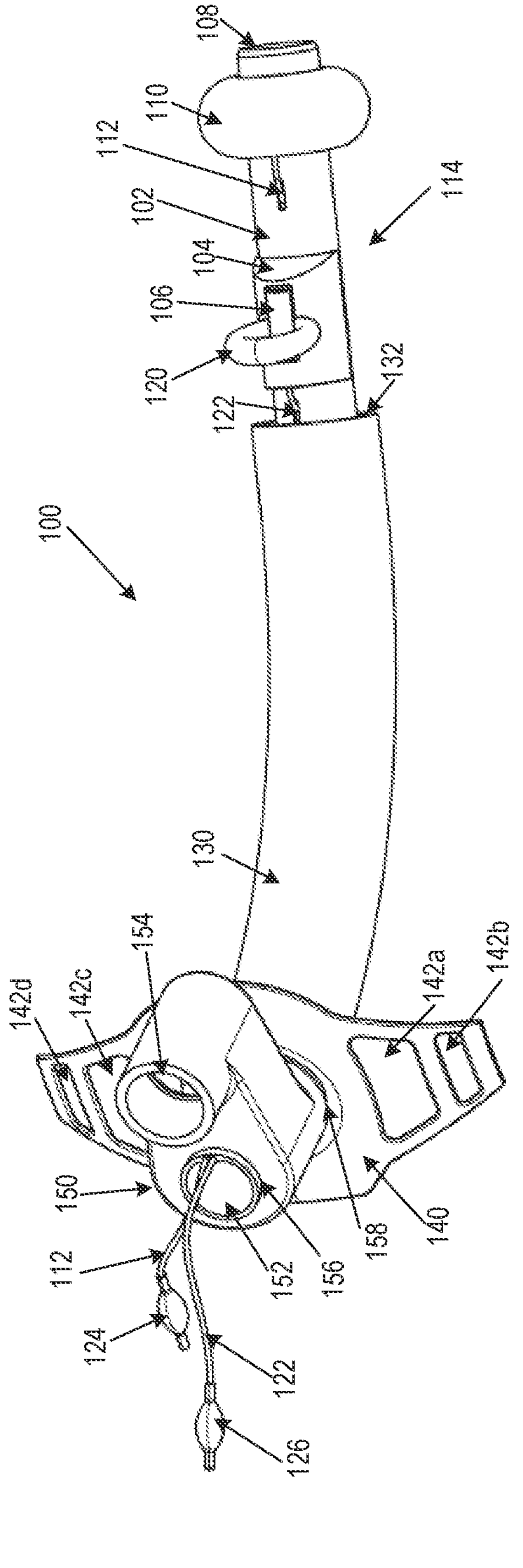
FIG. 1 illustrates a perspective view of an embodiment of an airway device.

FIG. 1 illustrates a perspective view of an embodiment of an airway device 100. The airway device 100 is a medical device configured for insertion in a patient's throat. In one embodiment, the airway device includes a scope channel 102 and an outertube 130. The outertube 130 is an elliptical shaped hollow tube configured to fit with the throat and hypopharynx of a patient. The outertube 130 forms an interior space that houses at least a portion of the scope channel 102. The outertube 130 may be designed to be semi-rigid/semi-flexible and may be made from a material that meets certain rigidity/flexibility requirements (such as, but not limited to, bending to efficiently fit within a patient's throat). In certain embodiments, the outertube 130 may comprise polymer tubing such as, but not limited to polyvinyl chloride (PVC), silicone, and/or other thermoplastic materials. In embodiments, portions of the semirigid portion of outertube 130 may comprise a corrugated configuration that allows for additional flexibility. The outertube 130 is sized and shaped to fit within the throat of a patient. The internal space in the outertube 130, i.e., the intraluminal space not occupied by the scope channel 102, provides a passageway for air flow to the patient.

The scope channel 102 is a flexible tubular structure that forms a circular or elliptical hollow channel. Similarly, to the outertube 130, the scope channel 102 may be designed to be semi-rigid/semi-flexible and may be made from a material that includes required rigidity/flexibility requirements (such as, but not limited to, bending to efficiently fit within a patient's throat). In certain embodiments, the scope channel 102 may comprise polymer tubing such as, but not limited to polyvinyl chloride (PVC), silicone, and/or other thermoplastic materials. In embodiments, portions of the semirigid portion of scope channel 102 may comprise a corrugated configuration to provide for additional flexibility.

An interior space of the scope channel 102 is configured to accommodate at least a gastroscope during a medical procedure. At a proximate end of the scope channel 102, an exterior, posterior surface of the scope channel 102 is affixed to an internal wall of the outertube 130. At a distal end, the scope channel 102 protrudes from a distal opening 132 of the outertube 130 and extends outwardly. At least this distal portion of the scope channel 102 is configured in shape and size to fit within the hypopharynx and esophagus of the patient.

In an embodiment, the external portion 114 of the scope channel 102 protruding from the outertube 130 includes an inflatable cuff 110. The inflatable cuff 110 is a torus shaped ring forming an inner hole, wherein the scope channel 102 fits within the inner hole. The cuff 110 may include a low volume, high pressure (LVHP) type cuff or a high volume, low pressure (HVLP) type cuff. The first type, an LVHP cuff, is made from stiffer, relatively inelastic materials. Due to its inherent stiffness, a greater level of pressure (50 cm $H_2O$ to 100 cm $H_2O$) is required to inflate the LVHP type cuff. The second type of cuff, the HVLP cuff, is composed of more elastic, compliant materials that inflates at lower pressures. To compensate for the lower pressure characteristics and create a seal against the tracheal wall, the diameter of an HVLP cuff is generally 1.5-2 times the diameter of the trachea when fully inflated. The inflatable cuff may also include a combination of both an LVHP type cuff and an HVLP type cuff as described in U.S. patent application Ser. No. 17/848,273 entitled, "SYSTEM AND METHOD FOR AN ENDOTRACHEAL TUBE CUFF ASSEMBLY," filed on Jun. 23, 2022, and incorporated by reference herein.

The cuff 110 is deflated when the airway device 100 is introduced into the patient and inflated after positioning of the cuff 110 in the esophagus of the patient. When inflated, the cuff 110 creates a seal against the esophageal wall and serves two important functions: 1. secure retention of the airway device 100 in the hypopharynx/proximal esophagus of the patient; and 2. prevent gastric reflux by mechanically blocking the gastric content from regurgitating into the pharynx and larynx.

In an embodiment, the external portion 114 of the scope channel 102 protruding from the outertube 130 also includes an inflatable bladder 120. The inflatable bladder 120 is positioned proximal to the inflatable cuff 110 and distal from the outertube 130. The bladder 120, in an inflated state, expands into a circular or ellipsoidal ring shape with an inner hole. An anterior portion of the inflated bladder 120 extends outwardly from the scope channel 102. A posterior portion of the ring is coupled to an anterior surface of the external portion 114 of the scope channel 102 along its transverse axis, e.g., along a circumferential line of the scope channel 102.

In an embodiment, the bladder 120 is attached to the scope channel 102 by a bladder base 104. The bladder base 104 may be affixed to an anterior surface of the external portion 114 of the scope channel 102 between the cuff 110 and the distal opening 132 of the outertube 130. A posterior surface of the bladder base 104 is configured to encircle at least partially an exterior surface of the scope channel 102. An anterior surface of the bladder base 104 is oval-shaped and forms an indentation that attaches to the inferior surface of the bladder 120. The bladder 120 lies transversely across this indentation of the bladder base 104.

Longitudinally spanning a top of the indentation is a bladder cover 106 with a distal end secured by attaching to the bladder base 104 and left unattached at a proximal end. The cover 106 covers the bladder 120 in a deflated state to provide a smoother surface for the airway device 100. This smoother surface facilitates the insertion process of the airway device 100 by allowing easier gliding of the airway device 100 into the throat of the patient. Without such a smooth surface, the inflating bladder, even deflated, may create an irregular surface, which could potentially catch the superior edge of the epiglottis leading to the epiglottis folding inferiorly and obstructing the inlet of the larynx, which could have a disastrous consequence Instead, the deflated bladder 120 is tucked into the indentation of the bladder base 104 and covered by the cover 106 creating a smooth surface. This smooth surface of the bladder base 104 facilitates the insertion of the airway device 100.

The cover 106 may include a material that has high elasticity, i.e., a material that is easily bendable and has a strong tendency to return to its original state. This way, when the bladder 120 is being inflated, the cover 106 bends up, due to its low flexural rigidity, to allow the inflated bladder 120 to be deployed from under the bladder cover 106. When the bladder 120 is inflated, the bladder cover 106 returns to its original place to cover the indented space and a posterior portion of the bladder 120, allowing a clear air passage without interference of the bladder cover 106. In another embodiment, a springe hinge may be attached to the bladder cover 106 and the bladder base 104 to hold the bladder cover 106 in a closed position.

At a proximal segment of the airway device 100, a flange 140 extends from the sides of the outertube 130. The flange 140 is configured for placement externally over a patient's mouth to stabilize the airway device 100. The flange 140 includes slits or holes 142*a-d* on opposing ends to attach cloth ties or a strap that wraps around the neck of the patient.

At a proximal side of the airway device 100, the scope channel 102 extends outward from the outertube 130. In an embodiment, an airway adapter 150 is attached to this proximal side of the airway device 100. The airway adapter 150 includes a first proximal mouth 156 that forms a seal around the proximal opening of the scope channel 102 extending from the outertube 130. A distal mouth of the airway adapter 150 is configured to sealingly fit over the outertube 130 including the scope channel 102. The endoscopic scope or other instruments may then be placed down the scope channel 102 and into the esophagus.

The airway adapter 150 further includes a second, proximal mouth 154 that forms a seal to an intraluminal space between the scope channel 102 and the outertube 130. The proximal mouth 154 is configured and sized for connecting to a ventilator or oxygen delivery tubing. The ventilator or oxygen delivery tubing may then provide air flow into the intraluminal space between the scope channel 102 and the outertube 130. The airway adapter 150 is optional. When the patient's respiratory status is satisfactory on room air and no assistance is necessary to breathe, the airway adapter 150 may not be used with the airway device 100.

A first inflation lumen 112 and a second inflation lumen 122 extend outward from the proximal opening of the scope channel 102. The first inflation lumen 112 is fluidly coupled to the bladder 120 for inflation and deflation while the second inflation lumen 122 is fluidly coupled to the cuff 110 for inflation and deflation. The pilot balloons 124 and 126 provide pressure and inflation indications for the bladder 120 and cuff 110 respectively.

In use, the airway device 100 provides a method for clearing the soft tissue from the larynx and hypopharynx of the patient. The airway device 100 is inserted into the patient and subsequently positioned such that the bladder 120 is adjacent to the larynx and hypopharynx of the patient. Once so positioned, the bladder 120 is inflated and expanded in a radial direction to ultimately form a circular or ellipsoid ring that forms an inner hole in the middle. The said radial expansion of the inflatable bladder 120 pushes the soft tissue that is normally present within the hypopharyngeal lumen adjacent to the laryngeal opening toward the periphery of the hypopharynx, to provide an unobstructed air passage into the trachea of the patient.

Figure 2:
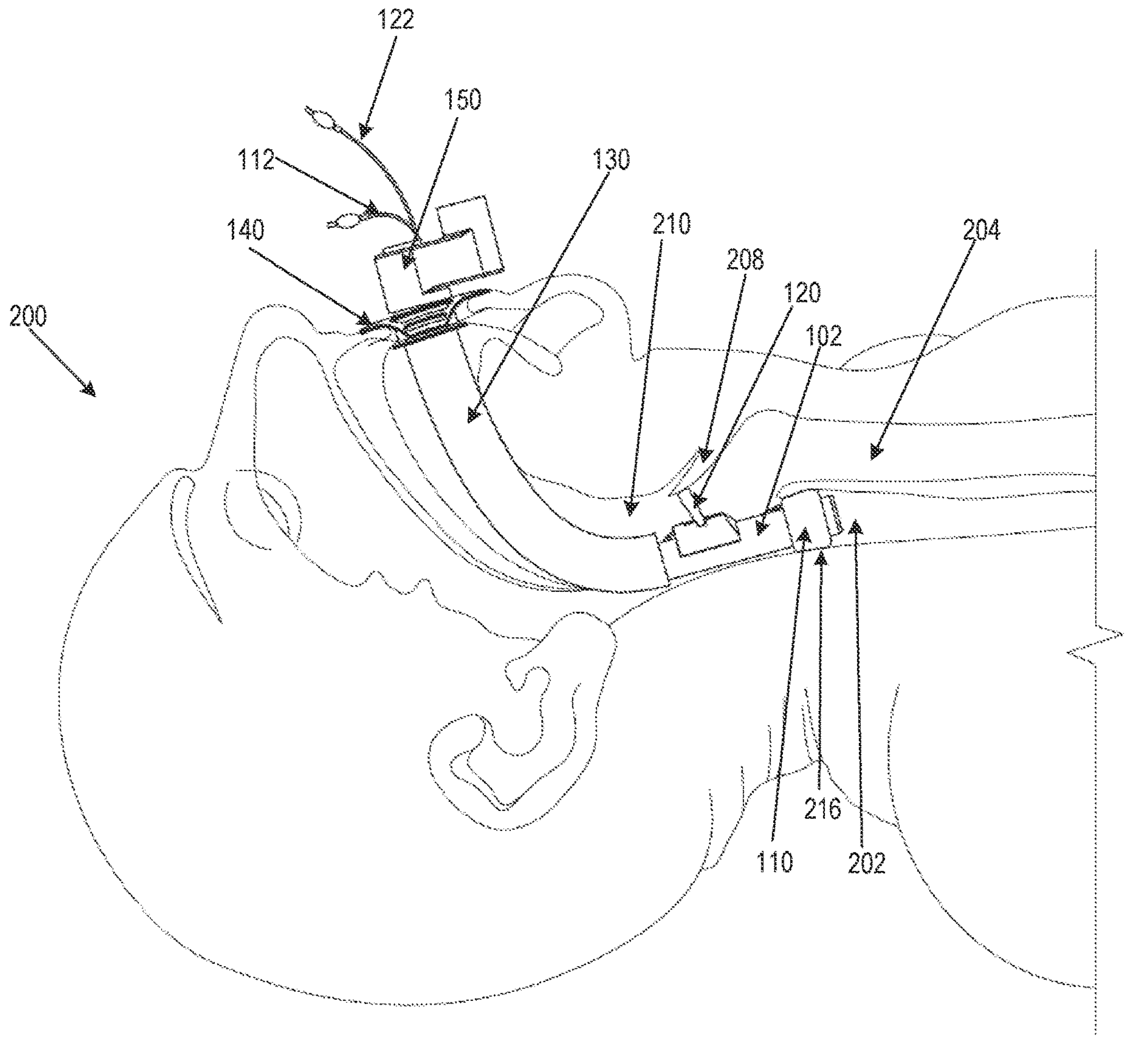
FIG. 2 illustrates an embodiment of the airway device positioned in vivo within a throat of a patient.

FIG. 2 illustrates an embodiment of the airway device 100 positioned in vivo within a throat of a patient 200. Though a human patient 200 is shown herein, the airway device 100 may be used on other animals as well.

The airway device 100 is configured to extend from the mouth of the patient into the hypopharynx 210 and into a proximal portion of the esophagus 202 of the patient 200. The cuff 110 is shown in an inflated state and is configured, e.g., in size, shape and pressure, to provide a seal against the esophageal wall 216. The presence of the cuff 110 at the distal end of the scope channel 102 prevents the gastric content or irrigating fluid from spilling into the trachea 204. The cuff 110, furthermore, eliminates the possibility of inadvertently spilling irrigating fluid during the insertion or removal of the scope and a foreign body falling into the airway.

The airway device 100 is also positioned such that the bladder 120 is adjacent to the larynx and hypopharynx 210 of the patient. Once so positioned, the bladder 120 is inflated and assumes a rigid, circular, or ellipsoidal ring shape. The inflatable bladder 120 expands in a radial direction to ultimately form a circular or ellipsoid ring with an inner hole in the middle. This radial expansion of the inflatable bladder 120 pushes the soft tissue that is normally present within the hypopharyngeal lumen adjacent to the laryngeal opening, including the epiglottis 208, toward the periphery of the hypopharynx, to provide an unobstructed air passage into the trachea 204 of the patient 200. The inner hole created in the middle of the inflated bladder 120 provides an unhindered air passage into the patient's trachea.

Figure 3:
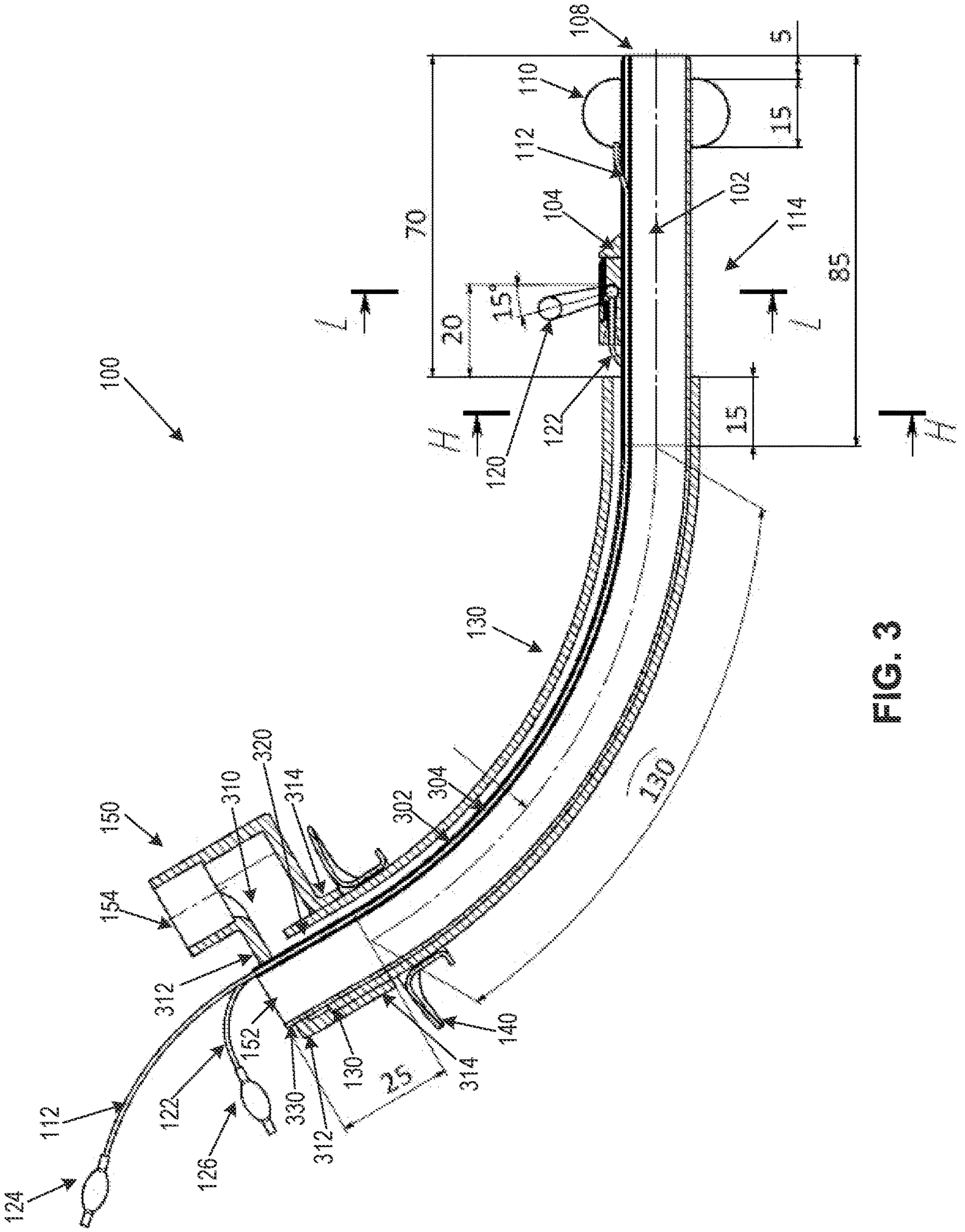
FIG. 3 illustrates an embodiment of a longitudinal, cross-sectional view of the airway device
Figure 4:
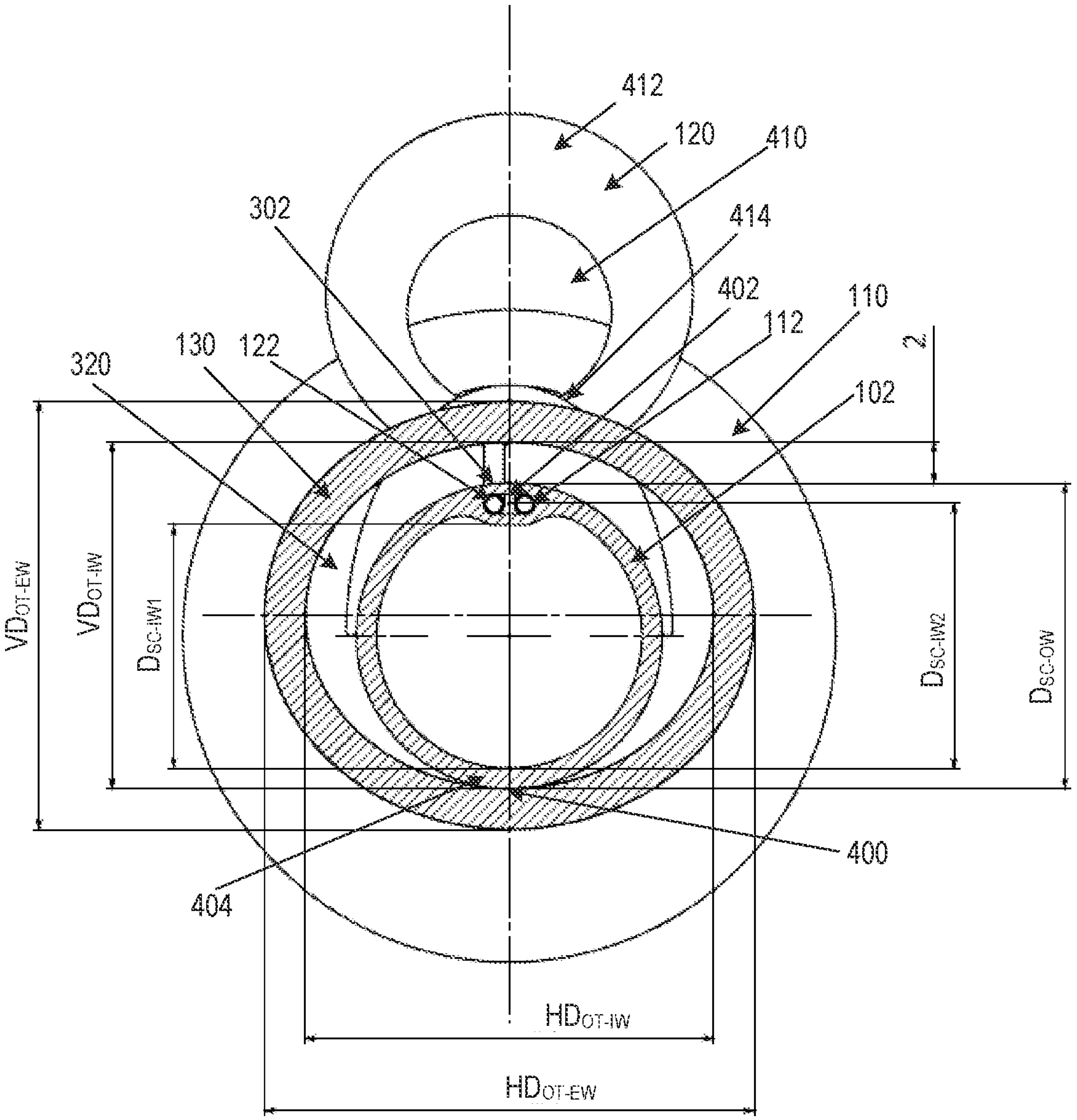
FIG. 4 illustrates an embodiment of a circumferential, cross-sectional view of the airway device.
Figure 5:
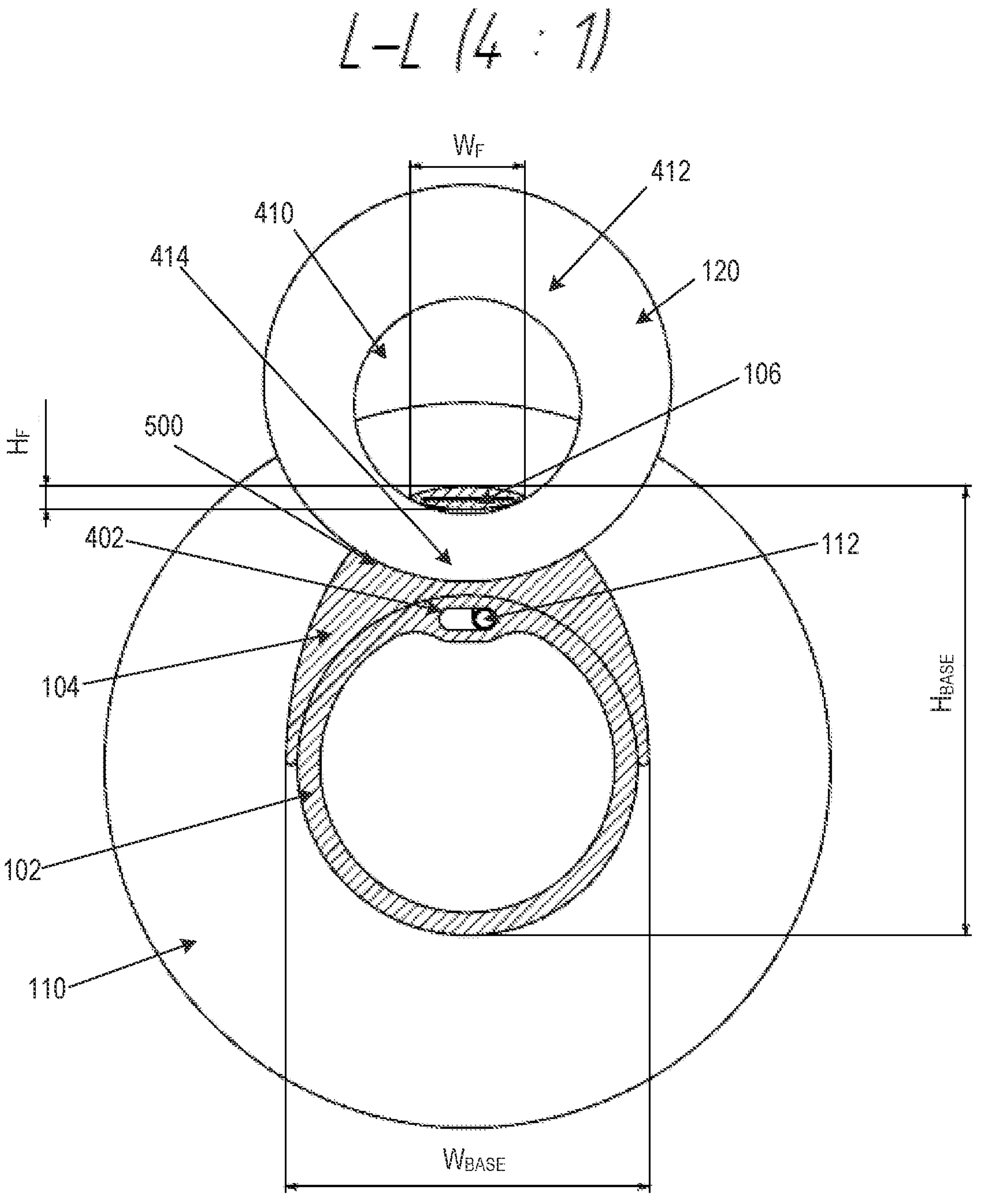
FIG. 5 illustrates an embodiment of another circumferential, cross-sectional view of the airway device.

FIGS. 3-5 illustrate various cross-sectional views of an embodiment of the airway device 100. Though the figures illustrate various dimensions and measurements, these dimensions and measurements are exemplary and may be varied, e.g., depending on the patient, use, or other factors. With respect to FIG. 3, a longitudinal cross-sectional view of the airway device 100 is illustrated including the scope channel 102, outertube 130, and airway adapter 150. At the scope channel 102, the first inflation lumen 112 and the second inflation lumen 122 extend through a hollow space formed in the anterior wall 302 of the scope channel 103 from the proximal opening of the scope channel 102 to the bladder 120 and cuff 110 respectively. Since the cuff 110 extends radially around the scope channel 102, the first lumen 122 that is fluidly coupled to the cuff 110 may alternatively be positioned within a posterior wall or lateral wall of the scope channel.

The outertube 130 encloses only a portion of the scope channel 102 proximal to the inflatable bladder 120 and distal from the proximal opening 152 of the scope channel 102. As seen in this cross-sectional view, proximally from the flange 140, a proximal portion 330 of the scope channel 102 extends outward from a proximal opening of the outertube 130. The airway adapter 150 includes a proximal top surface 312 that forms a proximal opening or mouth configured to sealingly fit around the proximal mouth 152 of the scope channel 102. A distal wall 314 of the airway adapter 150 forms a seal around the outertube 130. Between the proximal wall 312 and the distal wall 314, the airway adapter 150 forms a sealed air flow passageway or channel 310 that extends from the proximal mouth 154 to the intraluminal space 320 between an interior wall of the outertube 130 and an exterior wall of the scope channel 102. The tubular mouth 154 formed by the airway adapter 150 is configured and sized for connecting to a ventilator or oxygen delivery tubing. The ventilator or oxygen delivery tubing may thus insert oxygenated air into the intraluminal space 320. The oxygenated air will flow through the intraluminal space 320 and into the cleared airway in the hypopharynx of the patient.

The bladder 120, when inflated, is positioned transversely from the base 104 and extends outwardly and leans proximally from a top surface of the scope channel 102 and/or base 104. In particular, the bladder 120 leans at a proximate angle from a perpendicular line to an anterior surface of the scope channel 102. For example, the proximate angle may range from 0 to 30 degrees or range from 5 to 25 degrees or range from 10 to 20 degrees. This proximate angle is exemplary and may vary depending on such factors as a placement of the bladder 120 on the scope channel 102, an extension of the bladder 120 from the scope channel 102, the size of a throat of a patient, etc. A person of skill in the art, with this description, would understand that the dimensions of the bladder 120 and the angular positioning of the bladder 120 are configured to push and hold the soft tissue within the hypopharyngeal lumen adjacent to the laryngeal opening, including the epiglottis 208, toward the peripheral walls of the hypopharynx to provide an unobstructed air passage into the trachea of the patient.

In one example, the outertube 130 has a length $L_{OT}$ of 150 mm to 250 mm, and a thickness of 1 mm to 3 mm. The bladder base 104 has an exemplary length of 30 mm to 60 mm. The indentation or compartment within the bladder base 104 has an exemplary height of 2 mm to 4 mm and an exemplary length of 2 cm to 3 cm.

FIG. 4 illustrates a circumferential, cross-sectional view of the airway device 100 along the lines H-H shown in FIG. 3. As shown in FIG. 4, the circumference of the scope channel 102 is less than the circumference of the outertube 130 such that the scope channel 102 may fit internally to the outertube 130 while also leaving intraluminal space 320 between the scope channel 102 and the outertube 130. An external, posterior wall of the scope channel 102 is attached to or formed integrally with an internal, posterior wall of the outertube 130, at a line 400. As such, the intraluminal space 320 is greater at an anterior side of the airway device 100.

Within an anterior wall 302 of the scope channel 102, the first inflation lumen 112 and the second inflation lumen 122 extend through a hollow duct 402 formed in the anterior wall 302 of the scope channel 102. In an alternate embodiment, the duct 402 may be attached to an anterior, interior wall or to an anterior, exterior wall of the scope channel 102.

In one example, the outertube 130 may have a horizontal diameter $HD_{OT}$ that is greater than a vertical diameter $VD_{OT}$. For example, the external wall of the outertube 130 may have a horizontal diameter $HD_{OT\text{-}EW}$ in a range of 25-23 mm, or approximately 24 mm, and the external wall of the outertube 130 may have a vertical diameter $VD_{OT\text{-}EW}$ in range of 22-23 mm, or approximately 21 mm. The internal wall of the outertube 130 may have a horizontal diameter $HD_{OT\text{-}IW}$ in a range of 21-19 mm, or approximately 20 mm, and the interior wall of the outertube 130 may have a vertical diameter $VD_{OT\text{-}IW}$ in range of 18-16 mm, or approximately 17 mm. The outertube 130 is thus more oval shaped with a greater horizontal diameter than vertical diameter. The thickness of the wall of the outertube 130 is in a range of 3-5 mm, or approximately 4 mm.

In this example, the scope channel 102 is circular shaped with an outer wall diameter $D_{SC\text{-}OW}$ of 14-16 mm, or approximately 15 mm. To accommodate the hollow duct 402 in the anterior wall 302 of the scope channel 102, the thickness of the anterior wall 302 may be greater than a thickness of a posterior wall 404 of the scope channel 102. For example, the inner wall diameter $D_{SC\text{-}IW1}$ may be 12 mm at an anterior wall and the inner wall diameter $D_{SC\text{-}IW2}$ may be 13 mm at other portions.

The bladder 120 is a circular shaped ring in this example but may be elliptical shaped ring. The tubular ring of the bladder 120 creates an inner hole 410. A posterior portion 414 of the bladder 120 is attached to the bladder base 104 while the anterior portion 412 of the bladder 120 extends outwardly from the scope channel 102. An exemplary diameter of the outer circumference of the bladder 120 is approximately 10 mm to 20 mm. The exemplary diameter of the inner circumference of the bladder 120 is approximately 5 mm-10 mm. These dimensions and configurations of the bladder 120 are designed to enable the bladder 120 to reach and push the soft tissue and/or epiglottis to a periphery of the hypopharynx. A person of skill in the are would understand that these dimensions and configurations described herein are exemplary and may be varied to achieve the same purpose.

FIG. 5 illustrates a circumferential, cross-sectional view of the airway device 100 along the lines L-L shown in FIG. 3. The bladder 120 is shown in an inflated state with the bladder base 104. Disposed on the anterior aspect of the bladder base 104 is an indentation or compartment 500 that spans a full width along a transverse axis of the bladder base. A posterior portion 414 of the inflated bladder 120 is attached to and remains within the compartment 500 while the anterior portion 412 of the inflated bladder 120 extends outwardly from the bladder base 104. The cover 106 of the bladder base 104 lays flat in a closed position extending through the inner hole 410 of the bladder 120. The cover 106 covers a top portion of the compartment 500 forming two openings on opposing lateral sides for the anterior portion 412 of the bladder 120.

In one example, the compartment 500 has a height in a range of 2 mm to 4 mm and a length in a range of 2 cm to 3 cm. The width $W_F$ of the cover 106 is in a range of 4 to 6 mm, or approximately 5 mm, and the height HF of the cover 106 is in a range of 2 to 0.5 mm, or approximately 1 mm. In this example, the width $W_{BASE}$ of the bladder base 104 is 14 to 18 mm, or approximately 16 mm. The height of the scope channel 102 with the bladder base 104 is in a range of 22 to 18 mm, or approximately 20 mm.

Figure 6A:
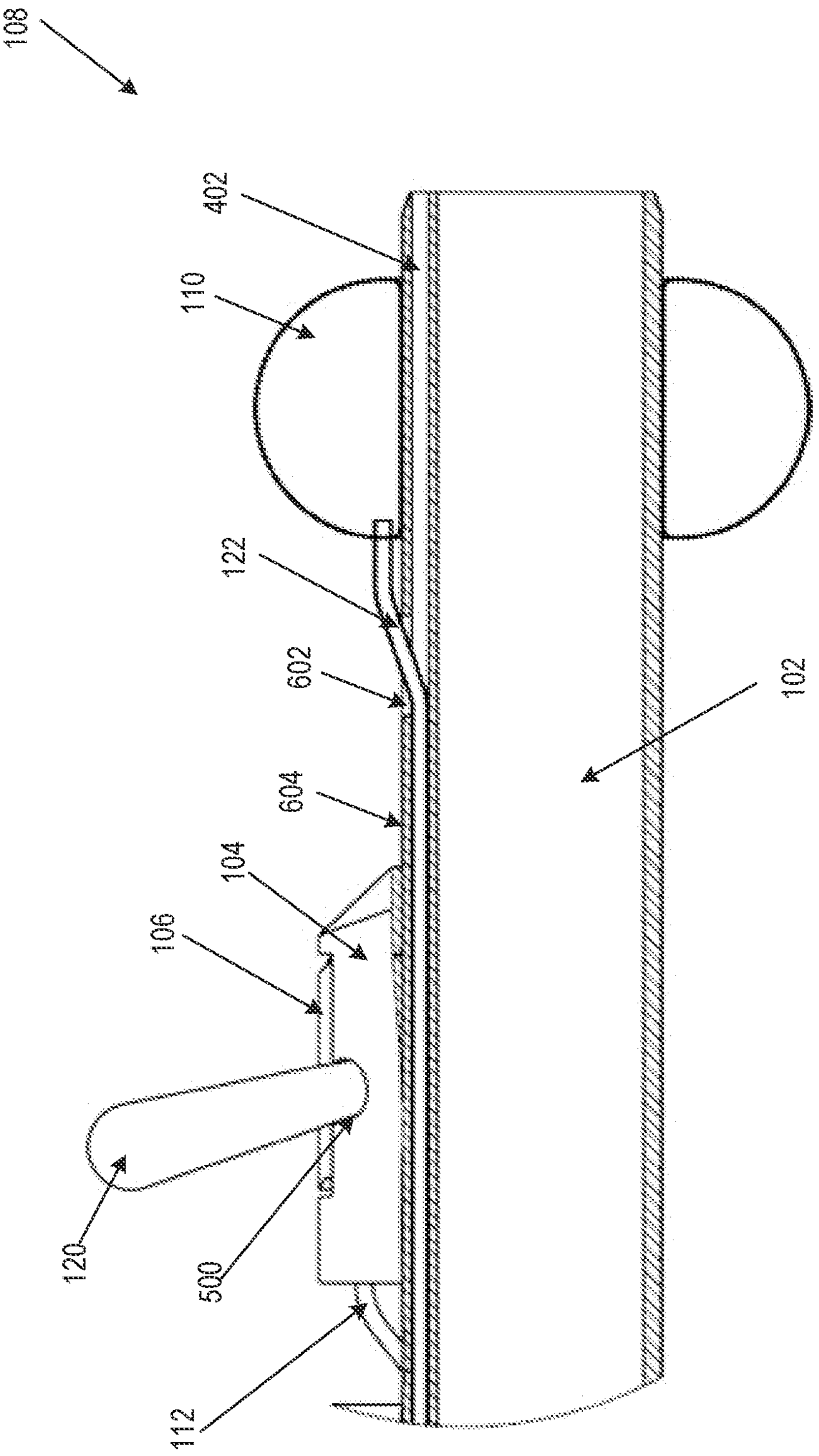
FIGS. 6A and 6B illustrate an embodiment of a distal portion of the scope channel 102 in more detail.
Figure 6B:
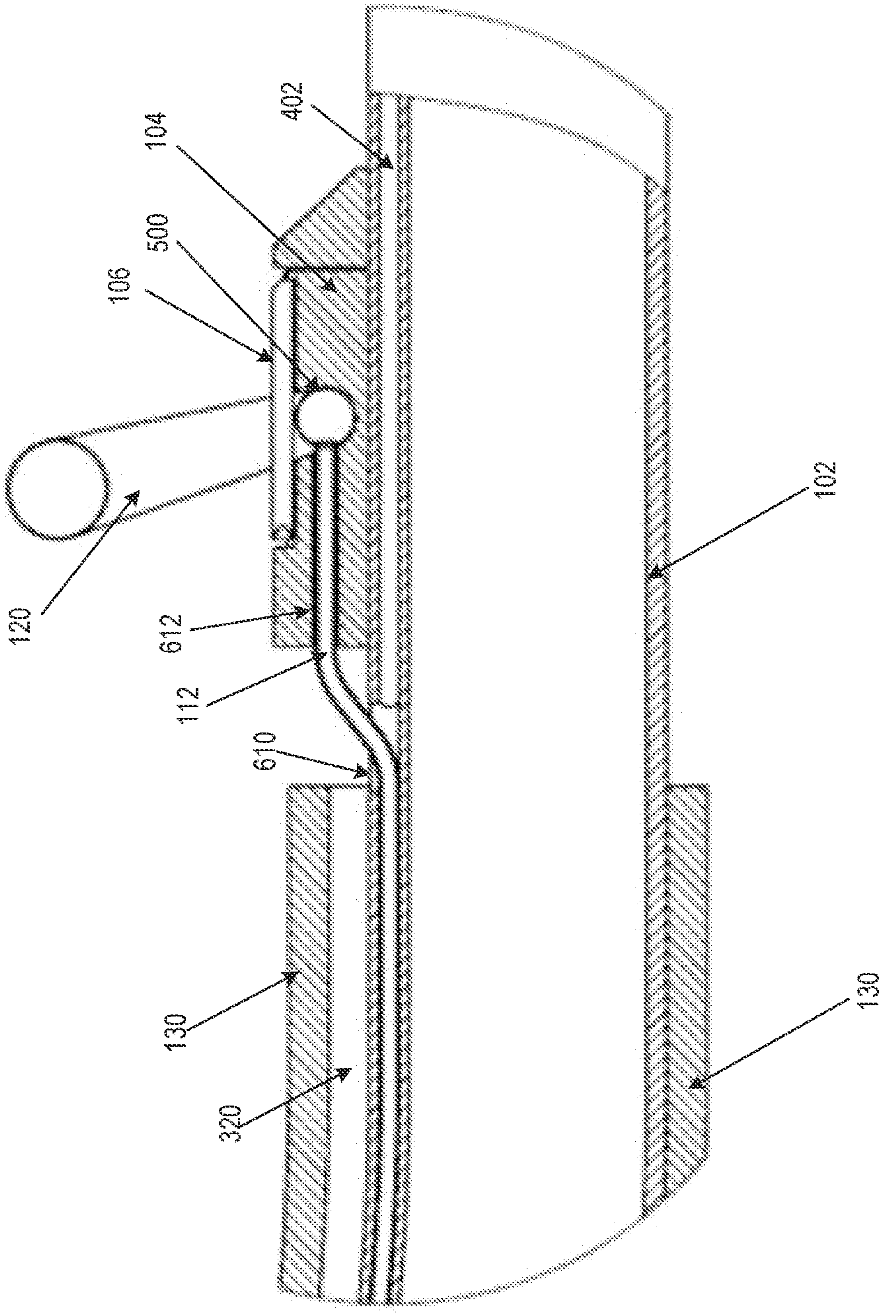

FIGS. 6A and 6B illustrate an embodiment of the distal, external portion 114 of the scope channel 102 in more detail, and, in particular, showing the first inflation lumen 112 and the second inflation lumen 122 in more detail. Referring first to FIG. 6A, the second inflation lumen 122 is fluidly coupled to the cuff 110 for inflation and deflation. An exterior wall 604 of the scope channel 102 forms an opening 602 for the second inflation lumen 122. The second inflation lumen 122 extends from the duct 402 through the opening 602 to fluidly couple with cuff 110.

Next, with respect to FIG. 6B, the first inflation lumen 112 is fluidly coupled to the bladder 120 for inflation and deflation. The exterior wall 604 of the scope channel 102 forms another opening 610 for the first inflation lumen 112. The first inflation lumen 112 extends from the duct 402 through the opening 610 to the bladder base 104. The bladder base 104 forms another duct 612 that extends from a proximal portion of the bladder base 104 to the bladder 120. The first inflation lumen 122 then fluidly couples with the bladder 120.

Figure 7A:
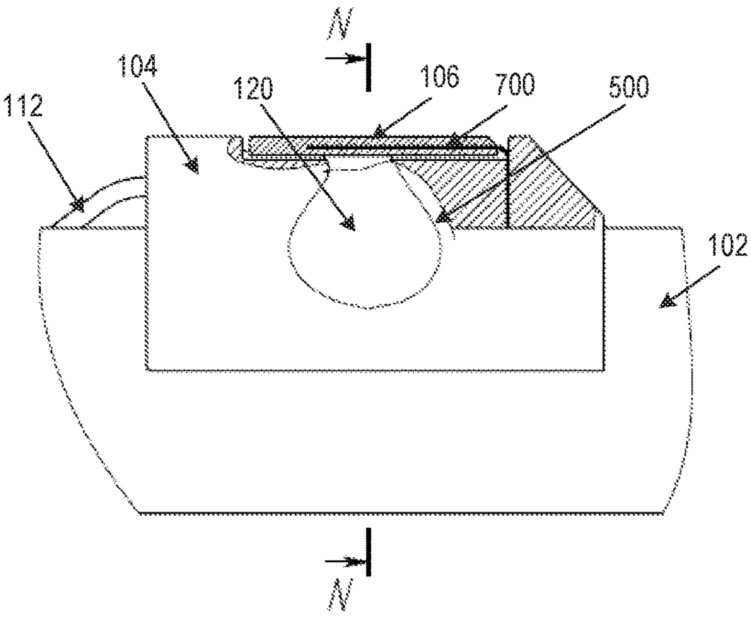
FIGS. 7A, 7B and 7C illustrate embodiments of the bladder base with the bladder in a deflated state.
Figure 7B:
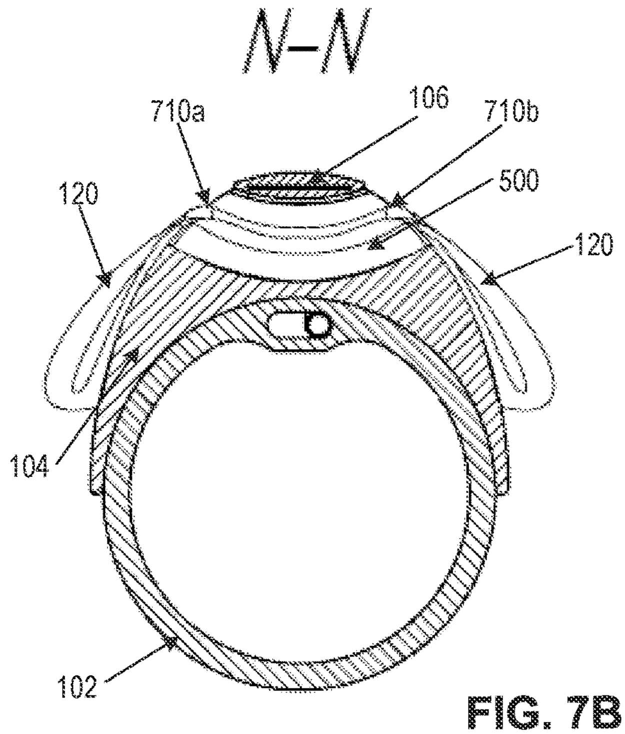
Figure 7C:
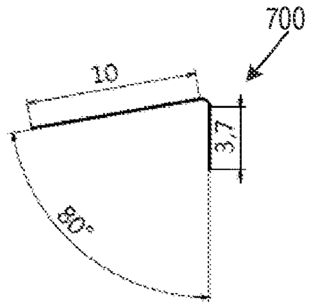

FIGS. 7A-7C illustrate embodiments of the bladder base 104 when the bladder 120 is in a deflated state. FIG. 7A illustrates the bladder base with the cover 106 in a closed position. FIG. 7B illustrates a cross-sectional view of the bladder base 104 along line N-N shown in FIG. 7A. FIG. 7C illustrates the hinge 700 of the cover 106 in a closed position. In an embodiment, the bladder base 104 forms two openings 710*a-b* on opposing lateral sides. The deflated bladder 120 extends through the compartment 500, with a first portion of the deflated bladder 120 extending from the first opening 710*a* and a second portion of the deflated bladder 120 extending from a second opening 710*b*. The cover 106 in a closed position extends across and covers an anterior opening to the compartment 500.

In an embodiment, a hinge 700 is positioned in the cover 106 and holds the cover 106 in a closed position. The hinge 700 includes one or more of a torsion spring, spring hinge, self-closing hinge, or another type of spring-loaded hinge. The hinge 700 automatically closes the cover 106 from an opened position and holds the cover 106 in a closed position.

Figure 8A:
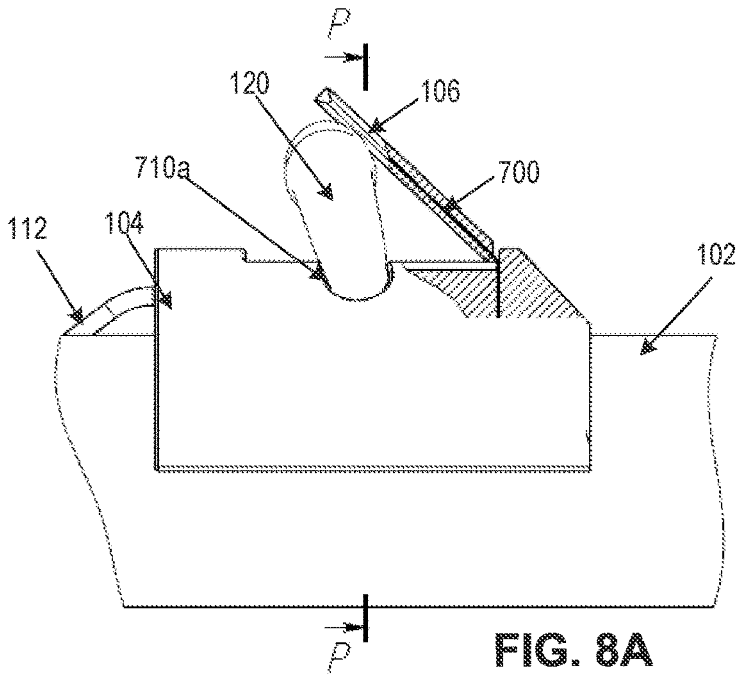
FIGS. 8A, 8B and 8C illustrate embodiments of the bladder base with the bladder in a semi-inflated state.
Figure 8B:
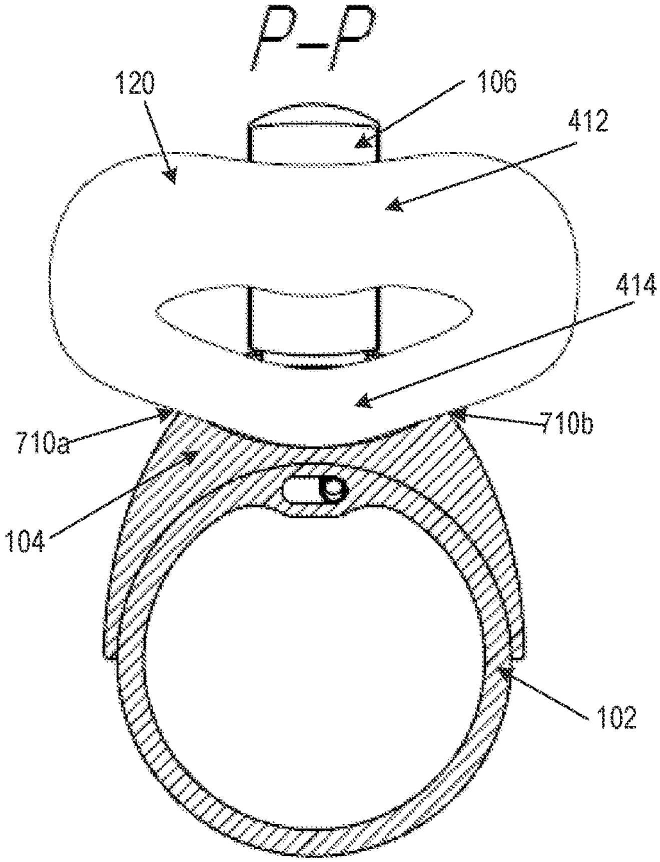
Figure 8C:
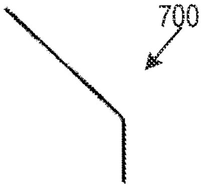

FIGS. 8A-8C illustrate embodiments of the bladder base 104 when the bladder 120 is in a semi-inflated state. FIG. 8A illustrates the bladder base with the cover 106 being forced partially open by the inflating bladder 120. FIG. 8B illustrates a cross-sectional view of the bladder base 104 along line P-P shown in FIG. 8A. FIG. 8C illustrates the hinge 700 of the cover 106 in the semi-open state of the cover 106. The hinge 700, e.g., a torsion of a spring in the hinge 700, is adjusted such that a force of the inflating bladder 120 is able to open the cover 106. When an anterior portion of the inflating bladder 120 expands past the cover 106, the hinge 700 automatically closes the cover 106.

Figure 9:
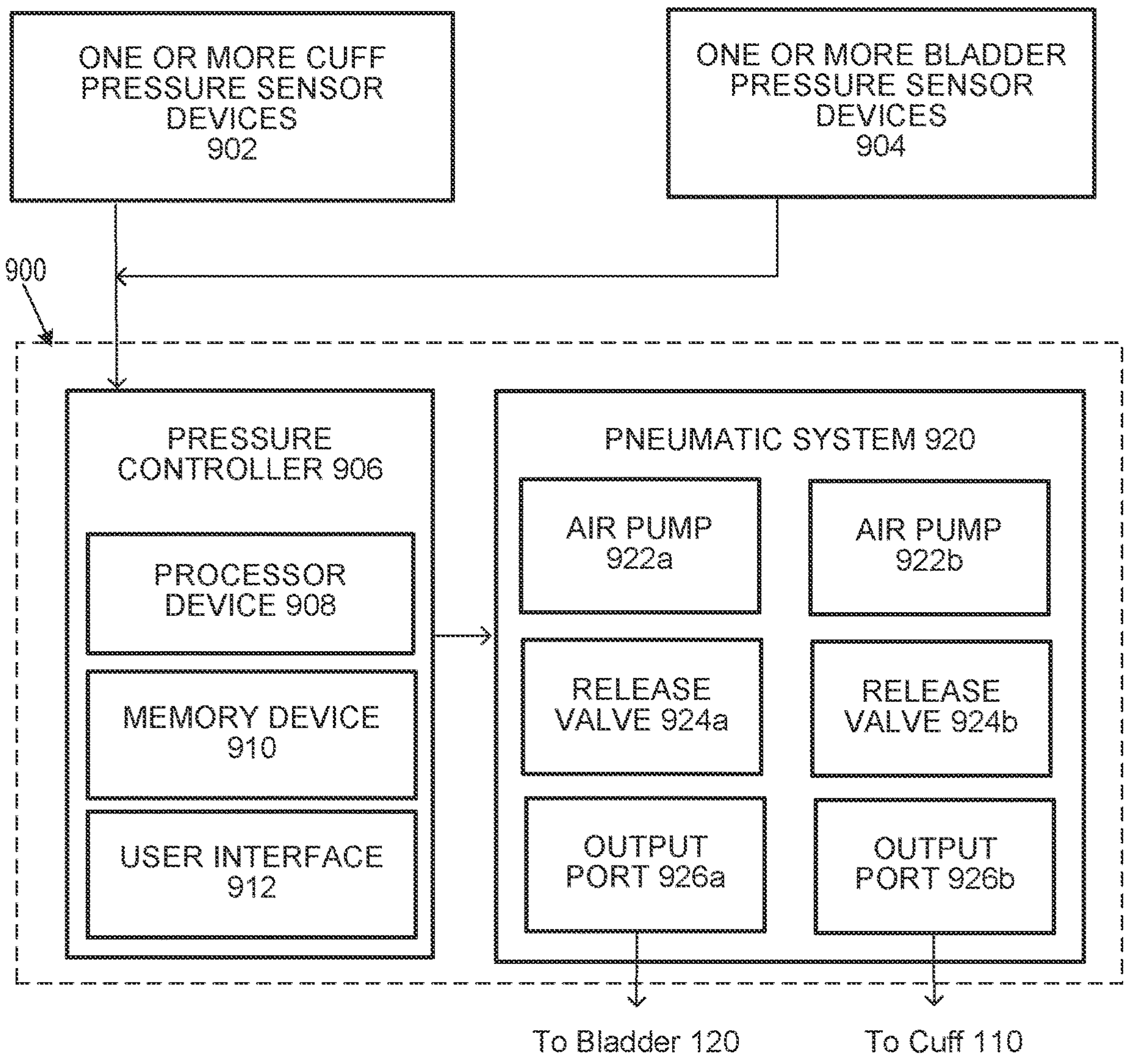
FIG. 9 illustrates a schematic block diagram of an exemplary embodiment of a pressure regulator and control system.

FIG. 9 illustrates a schematic block diagram of an exemplary embodiment of a pressure regulator and control system ("regulator system") 900 for the airway device 100. The regulator system 900 fluidly communicates with and inflates and adjusts the pressure within the cuff 110 and/or the bladder 120, e.g., when the airway device 100 is implanted into the patient. The regulator system 900 may monitor and control the pressure of the cuff 110 and the bladder 120 individually and separately.

The regulator system 900 includes a pressure controller 006 and pneumatic system 920. The pressure controller 906 includes a processor device 908 and a memory device 910. The memory device 910 sores instructions which when executed by the processor device 908 or other components of the regulator system 900, causes the regulator system 900 to perform one or more functions described herein. The processor device 908 includes at least one processing circuit, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The memory device 910 includes a non-transitory memory device and may be an internal memory or an external memory and may be a single memory device or a plurality of memory devices. The memory device 910 may be a read-only memory, random access memory, volatile memory, non-volatile memory, static memory, dynamic memory, flash memory, cache memory, and/or any non-transitory memory device that stores digital information.

The pressure controller 906 may be co-located with the pneumatic system 920 in a same physical device or located separately in a different device, such as a user device or other processing device. The pressure controller 906 further includes a user interface 912. The user interface 912 generates user input and output (I/O) and includes one or more of a display, keyboard, touch screen, mouse, touchpad, gauge, switch, or other I/O device.

In operation, desired predetermined pressure settings are determined for the cuff 110 and the bladder 120 by the pressure controller 906 in response to user input received by the user interface 912. Alternatively, one or more default pressure settings may be implemented, e.g., in absence of user input. A different pressure setting may be set for the cuff 110 and bladder 120. The pressure setting may be a predetermined pressure or in a pressure range, e.g., typically within a plus or minus 5 cm $H_2O$. For example, when the cuff 110 is a low volume, high pressure (LVHP) type cuff, the pressure setting for the cuff 110 is typically within the range of 50 cm $H_2O$ to 150 cm $H_2O$. When the cuff 110 is a high volume, low pressure (HVLP) type cuff, the cuff 110 is typically within the range of 10 cm $H_2O$ to 20 cm $H_2O$.

In contrast, the pressure setting for bladder 120 may be a pressure (plus or minus 5 cm $H_2O$) within the range of 10 cm $H_2O$ to 50 cm $H_2O$. The cuff 110 and the bladder 120 may thus operate in different pressure ranges. The pressure controller 906 further determines a frequency of measuring and adjusting the pressure of the cuff 110 and the bladder 120, such as through a user input or default setting.

The pneumatic system 920 includes a first pneumatic pathway for the bladder 120 that includes, e.g., a first air pump 922*a* and release valve 924*a* that fluidly couples with the bladder 120 through, e.g., output port 926*a*, pilot balloon 124 and lumen 112. The pneumatic system 920 further includes a different, second pneumatic pathway for the cuff 110 that includes a second air pump 922*b* and release valve 924*b* that fluidly couples with the cuff 110 through, e.g., output port 926*b*, pilot balloon 126 and lumen 122. Though two air pumps 922*a*, 922*b* are described herein, a single air pump may be implemented that includes a valve or switch between the two fluid pathways. The pneumatic system 920 thus includes separate pneumatic pathways to fluidly increase or decrease the pressure in the cuff 110 and the bladder 120 independently and separately.

In operation, the pressure controller 906 receives pressure measurements from one or more pressure sensor devices 902, 904 to measure the internal pressures of the cuff 110 and the bladder 120. One of the cuff pressure sensor devices 902 may be positioned on an outer surface of the cuff 110 to measure tracheal wall pressure. Additional pressure sensor devices may also be implemented. The pressure sensor devices 902, 904 generate and communicate pressure measurements to the pressure controller 906 through a wired lead and/or a wireless transmitter.

The regulator system 900 includes a pressure feedback loop wherein the pressure controller 906 controls the pneumatic system 920 to adjust the pressures for cuff 110 and the bladder 120, separately, responsive to the pressure measurements. The pressure controller 906 signals the pneumatic system 920 to add or release air to the bladder 120 and/or the cuff 110. For example, to adjust the pressure in the bladder 120 the pressure controller 906 may signal the air pump 922*a* to add air to the bladder 120 or signal the release valve 924*a* to release air from the bladder 120. In another example, to adjust the pressure in the cuff 110, the pressure controller 906 signals the air pump 922*b* to add air to the cuff 110 or signal the release valve 924*b* to release air from the cuff 110.

The regulator system 900 monitors the pressure measurements and adjusts the pressure of the cuff 110 and the bladder 120, automatically to achieve the predetermined pressure settings. The pressure controller 906 may monitor and adjust the pressures of the cuff 110 and the bladder 120 continuously or may monitor and adjust the pressures at predetermined intervals. The regulator system 900 may further include visible and/or audible alarms in the event of unsafe pressure measurements.

Figure 10A:
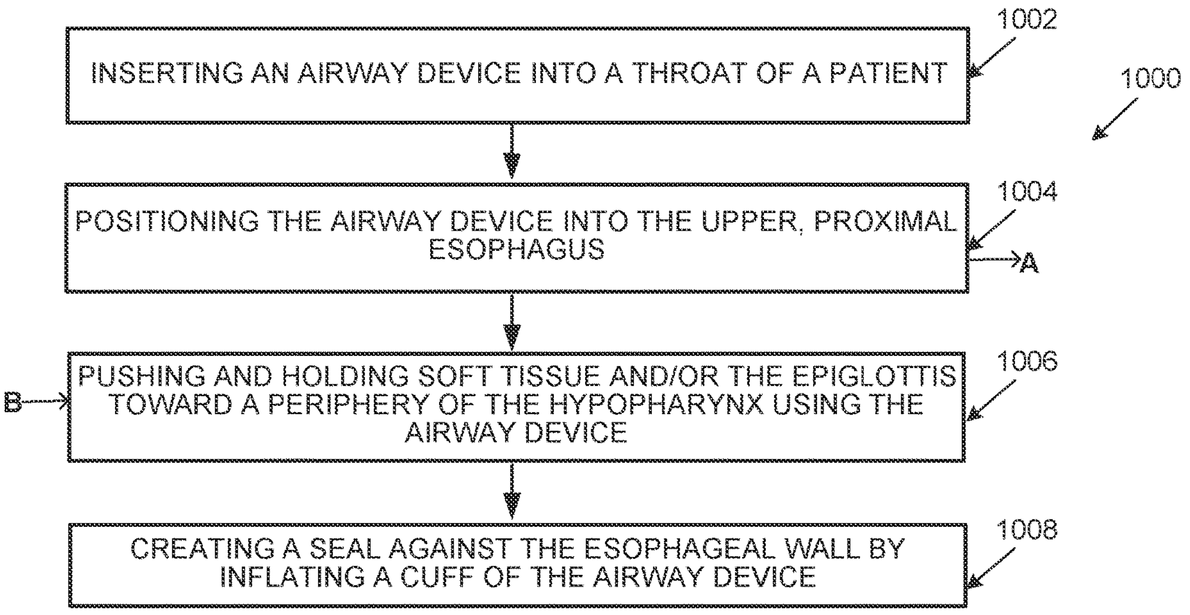
FIGS. 10A, 10B, 10C and 10D illustrate embodiments of methods of the airway device during a gastroscopic procedure.

FIGS. 10A-D illustrate embodiments of methods of the airway device 100 for clearing soft tissue to establish an open airway and maintaining the open airway during gastroscopic procedures. Referring first to FIG. 10A, a method 1000 for insertion of the airway device is described. Initially, at step 1002, the airway device 100 is inserted into a throat of a patient. A gastroscope may be pre-inserted through the scope channel 102. After insertion of the airway device 100 at 1002, the airway device 100 is subsequently positioned at 1004 to place the bladder 120 adjacent to a larynx and hypopharynx of the patient and to place the cuff 110 into the upper esophagus. The positioning of the airway device 100 may be facilitated by utilizing a pre-inserted gastroscope as a guide, as described in more detail with respect to FIG. 11.

Once so positioned, at step 1006, the bladder 120 is inflated and expands outwardly in a radial direction to ultimately form a circular or ellipsoid ring having an inner hole. This radially expanding bladder 120 pushes the epiglottis and the soft tissue within the hypopharyngeal lumen (and adjacent to the laryngeal opening) toward the periphery to provide a more unobstructed air passage into the trachea. The inner hole of the inflated bladder 120 provides an unhindered air passage into the patient's trachea.

Though a bladder 120 is described herein, other mechanisms may be employed to push the epiglottis and other soft tissue toward the anterior wall of the hypopharynx. Though an inflatable bladder 120 is described herein, other mechanisms may be employed to push the epiglottis and other soft tissue toward the anterior wall of the hypopharynx during a gastric procedure. For example, a circular or ellipsoidal plastic or rubber ring may be attached to an outside of the scope channel 102 by a hinge. The ring may lay relatively flat against the scope channel 102 during insertion. The hinge may then be activated after insertion of the airway device 100 to deploy the ring which then pushes the epiglottis and other soft tissue toward the anterior wall of the hypopharynx. Other mechanisms may include a thin, rectangular rubber or plastic member attached by a hinge to the scope channel 102. The rectangular member when deployed by the hinge extends across the hypopharynx to push the epiglottis and other soft tissue. A person of skill in the art would appreciate that these and other mechanisms may be implemented for the purpose of pushing the epiglottis and other soft tissue toward the anterior wall of the hypopharynx during a gastric procedure.

At 1008, the cuff 110 is inflated in the proximal esophagus to create a seal between the cuff 110 and the esophageal wall. The seal is in some embodiments a watertight seal. The inflated cuff 110 helps to maintain a separation of the digestive tract and the airway. For example, the presence of the cuff 110 helps to prevent gastric content from spilling into the airway. The cuff 110, furthermore, helps to eliminate the possibility of inadvertently spilling irrigating fluid (used to cleanse the gastroscope) into the airway, such as during the insertion or removal of the airway device 100.

Figure 10B:
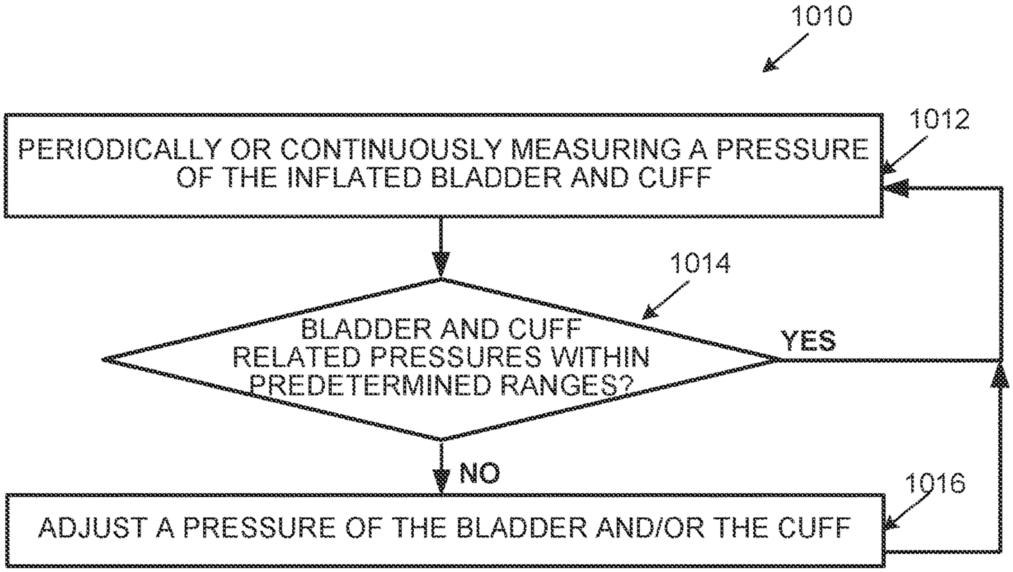

FIG. 10B illustrates an embodiment of a method 1010 for maintaining the airway device 100 during a procedure. After insertion and inflation, the endoscopic procedure is performed customarily. During the procedure, the pressures within the cuff 110 and the bladder 120 are maintained within first and second predetermined ranges respectfully. For example, the cuff 110 is maintained within a first predetermined pressure range that maintains a good seal with the esophageal wall but without unduly harming the esophageal wall. In addition, the bladder 120 is maintained within a second predetermined pressure range such that the bladder 120 effectively holds the epiglottis and the soft tissue toward the periphery of the hypopharyngeal lumen without harming the soft tissue or epiglottis.

At step 1012, one or more pressure measurements relating to the cuff 110 and bladder 120 are obtained from one or more pressure sensor devices. The one or more pressure sensor devices may measure the esophageal wall pressure, e.g., the pressure exerted by the cuff 110 on the wall of the esophagus. In another example, one or more pressure sensor devices may measure the pressure exerted by the bladder 120 on the soft tissue or epiglottis in the hypopharynx. The one or more pressure sensor devices may measure the pressures within the bladder 120 and/or the cuff 110. These pressure measurements may be determined periodically or continuously.

Using these pressure measurements, it is determined (e.g., by the pressure controller 906) at 1010 whether the pressure measurements relating to the bladder 120 is within a first predetermined range and/or whether the pressure measurements relating to the cuff 110 is within a second predetermined range at 1014. If the pressure measurements are within the predetermined ranges, then the method 1000 continues to monitor the pressures periodically or continuously with respect to the cuff 110 and/or the bladder 120.

When the esophageal wall or cuff pressure is greater than or less than the first predetermined pressure range, the pressure in the cuff 110 is adjusted at step 1016. In addition, when the pressure exerted by the bladder 120 or the bladder internal pressure is greater than or less than the second predetermined pressure range, the pressure in the bladder 120 is adjusted at step 1016. These steps may be performed at preset intervals or continuously. The pressure of the cuff 110 and the bladder 120 are thus controlled separately using separate pneumatic pathways.

Figure 10C:
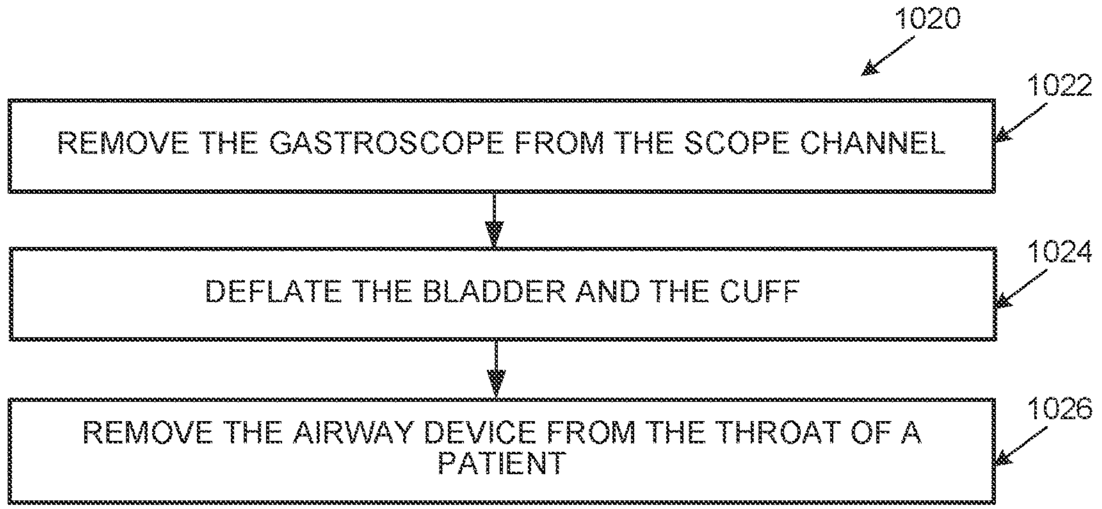

FIG. 10C illustrates a method for removal of the airway device 100. At a conclusion of the gastroscopic procedures, the gastroscope is withdrawn from the scope channel 102 at 1022, and the cuff 110 and the bladder 120 are deflated at step 1024. The airway device 100 is then removed from the throat of the patient at 1026.

Figure 10D:
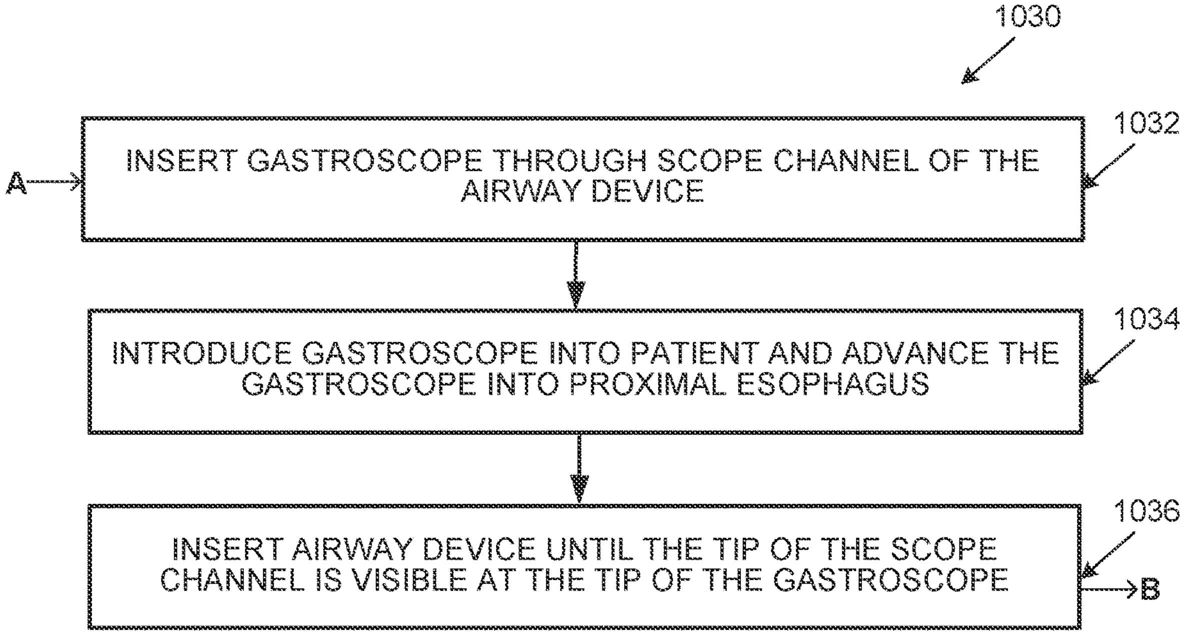

FIG. 10D illustrates an embodiment of a method 1030 for positioning the airway device 100 in a patient in more detail. The insertion of the airway device 100 is of paramount importance given the delicate nature of the upper aerodigestive tract and the limited available space in the pharynx and the larynx. The airway device 100 is preloaded with a gastroscope by inserting the gastroscope through the scope channel 102 at step 1032. The airway device 100 is slid away from the distal tip of the gastroscope such that there is enough length for the insertion portion of the gastroscope to be exposed. The gastroscope is then introduced into the patient and advanced into the proximal esophagus at step 1034. With the gastroscope held firmly in place, the airway device 100 is advanced until the scope channel 102 is inserted into the hypopharynx/proximal esophagus and the tip of the scope channel 102 is visible at the tip of the gastroscope at 1036. This ensures that the cuff 110 on the scope channel 102 is properly positioned within the proximal esophagus. Once the airway device 100 is so inserted, it is stabilized by inflating the cuff 110.

In an embodiment, the scope channel 102 includes clear or translucent material such that the bladder 120 may be visible to the gastroscope. The gastroscope may be pulled into the scope channel to ensure proper placement of the bladder 120. This step may be performed before and/or after inflation of the bladder 120.

The airway device 100 has multiple advantages to ease the insertion process. In a first advantage, the bulkiness of the airway device 100 is minimized through a compact design. For example, the outertube 130, a conduit for the airflow, is configured to house the scope channel 102 within its tube lumen. This configuration, compared to having two separate tubes, minimizes the cross-sectional area of the tubular portion of the airway device 100.

Second, the inflating bladder 120 is in a deflated state during the introduction of the device into the patient. In the deflated state, prior to introduction, the bladder 120 is deflated and folded under the cover 106. With the bladder volume so minimized, the insertion of the airway device 100 is greatly facilitated. The smooth device surface enabled by the provision of the bladder cover 106 that tucks away the bladder 120 allows easy gliding of the airway device 100. Without such a provision, the bladder 120, even deflated, would create an irregular surface, which can potentially catch the superior edge of the epiglottis leading to the epiglottis folding inferiorly and obstructing the inlet of the larynx. The occlusion of the inlet of the larynx can have catastrophic consequences, even death. To avoid these untoward eventualities, the airway device 100 is equipped with the bladder cover 106 which simultaneously covers the bladder 120 and creates a smooth surface.

Third, the introduction and advancement of the airway device 100 are facilitated by utilizing the pre-inserted gastroscope as its guide. Successful insertion of any device into the upper aerodigestive tract, above all, requires a clear pathway. Achieving this step is challenging because when the patient is placed under deep sedation, the laryngopharyngeal structures become flaccid and collapse, resulting in complete or partial blockage of the airway. With the novel device and method disclosed herein, the successful introduction of the airway device 100 into the upper aerodigestive tract is secured.

Figure 11:
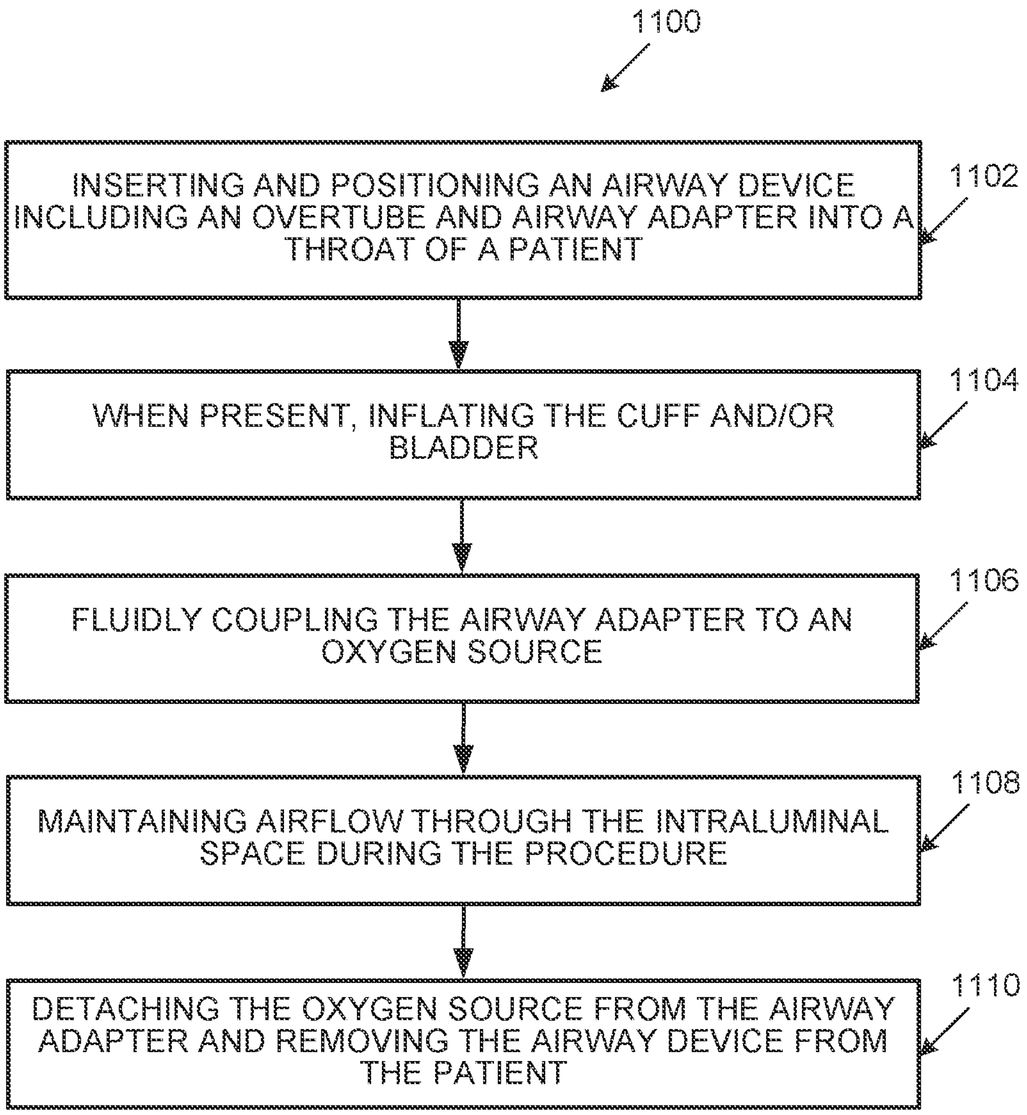
FIG. 11 illustrates an embodiment of a method of the airway device for delivering oxygenated air to a patient during a gastroscopic procedure.

FIG. 11 illustrates an embodiment of a method of the airway device 100 for delivering oxygenated air and maintaining ventilation of a patient during gastroscopic procedures. In this embodiment, the airway device 100 includes at least the outertube 130 and airway adapter 150, described herein. The airway device 100 may also include the bladder 120 and/or the cuff 110. The airway adapter 150 includes the tubular mouth 154 that is configured and sized for connecting to a ventilator or other oxygen delivery source. The airway adapter 150 is attached to the outertube 130 creating a fluid coupling through the sealed air flow passageway 310 with the intraluminal space 320 between the scope channel 102 and the outertube 130. The flow of oxygenated air into the patient's lungs is enhanced by inflating the soft tissue-clearing bladder 120, which results in the formation of a patent air passage. If necessary, ventilator-assisted ventilation is achieved by connecting the tubular mouth 154 of the airway adapter 150 to a ventilator. The oxygenated air flows through the sealed air flow passageway 310 into the intraluminal space 320.

The method 1100 includes at 1102 inserting and positioning the airway device 100 in the throat of the patient. If present, the cuff 110 is positioned in the upper esophagus and is inflated at 1104. In addition, if present, the bladder 120 is positioned adjacent to the larynx and hypopharynx of the patient and also inflated at 1104. The tubular opening 154 of the airway adaptor is fluidly coupled with an oxygen source at 1106. The oxygen source may include a ventilator or other pressurized oxygen source. During the procedure, the airflow is maintained through the intraluminal space 320 and into the trachea of the patient at 1108. At a conclusion of the procedure, the oxygen source is detached from the airway adapter 150, and the airway device 100 is removed from the patient at 1110.

The airway device 100 may have various embodiments depending on the needs of a patient. For example, an added airway adapter 150 may not be necessary when the patient needs no respiratory aid. In another embodiment, the scope channel 102 may include the cuff 110 to prevent gastric contents or irrigating fluid from leaking into the trachea, but not include the bladder 120. In another embodiment, the scope channel 102 may include the bladder 120 to preserve an open airway during the medical procedure, but not include the cuff 110.

The esophageal cuff 110 prevents gastric reflux by mechanically blocking the gastric content from regurgitating into the pharynx and larynx. The inflated bladder 120 forms a circular or ellipsoidal ring configured to retract the soft tissue and/or the epiglottis from the center to the periphery of the hypopharynx adjacent to the laryngeal opening and thus clear an airway for a patient. In addition, the inner hole 410 formed in the middle of the inflated bladder 120 provides an unhindered air passage into the patient's trachea. The airway adapter 150 and outertube 130 provide another airway to the trachea by creating the sealed air flow passageway 310 to the intraluminal space 320 between the scope channel 102 and the outertube 130. The passageway 310 may be enhanced by connecting the airway adapter 150 to an oxygen source. The airway device 100 provides many advantages in different configurations.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled," "coupled to," "connected to" and/or "connecting" or "interconnecting" includes direct connection or link between nodes/devices and/or indirect connection between nodes/devices via an intervening item. As may further be used herein, inferred connections (i.e., where one element is connected to another element by inference) includes direct and indirect connection between two items in the same manner as "connected to." As may be used herein, the terms "substantially" and "approximately" provide an industry-accepted tolerance for its corresponding term and/or relativity between items.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above regarding particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied, or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A medical device, comprising:

a scope channel configured for insertion into a proximal esophagus of a patient;

an inflatable cuff positioned on a distal portion of the scope channel and configured for insertion into the proximal esophagus of the patient, wherein the scope channel is positioned within an inner hole formed by the inflatable cuff; and an inflatable bladder positioned proximally to the inflatable cuff on the scope channel and configured for positioning substantially proximal to the esophagus of the patient such that the inflatable cuff and the inflatable bladder are non-overlapping, wherein, in an inflated state, the inflatable bladder forms a ring having an outer circumference and an inner circumference, wherein the ring is positioned substantially anterior to the scope channel, wherein a posterior portion of the outer circumference of the ring is attached to an anterior surface of the distal portion of the scope channel, wherein the inner circumference of the ring forms an inner hole, and wherein an anterior portion of the outer circumference of the ring extends outwardly at a proximate angle from the anterior surface of the scope channel, wherein the anterior portion of the outer circumference of the ring is configured to contact and retract an epiglottis of the patient from a center to a periphery of a hypopharynx of the patient, wherein the inner hole of the ring is configured to form an air passageway and allow air to pass into a trachea of the patient, wherein the ring is external and anterior to the scope channel.

2. The medical device of claim 1, when the inflatable bladder is in a deflated state, the ring and the inner hole of the ring collapse and fold for ease of insertion.

3. The medical device of claim 1, wherein the inner hole of the ring, when the inflatable bladder is in an inflated state, is positioned between the retracted epiglottis and the anterior surface of the distal portion of the scope channel to provide the air passage into the trachea.

4. The medical device of claim 3, wherein the scope channel further comprises a bladder base configured to attach the posterior portion of the outer circumference of the ring to the anterior surface of the distal portion of the scope channel, wherein the bladder base includes:

a posterior surface of the bladder base coupled to the anterior surface of the distal portion of the scope channel; and an anterior surface of the bladder base coupled to the posterior portion of the outer circumference of the ring.

5. The medical device of claim 4, wherein the bladder base further comprises:

an indentation formed in the bladder base that spans the anterior surface of the bladder base, wherein the indentation is configured to hold the inflatable bladder in a deflated state along a transverse axis of the bladder base;

a cover attached by a spring hinge to a distal portion of the bladder base, wherein the cover, with the inflatable bladder in a deflated state, extends along a top portion of the indentation to cover the inflatable bladder within the bladder base;

wherein a proximal end of the cover is configured to open in response to an upward force exerted by the inflatable bladder during inflation to allow deployment of the inflatable bladder; and wherein the cover, after the deployment of the inflatable bladder, by a recoil action of the spring hinge, extends through a lower portion of the inner hole of the ring of the inflatable bladder in an inflated state and over the indentation.

6. The medical device of claim 5, wherein the indentation of the bladder base is configured to hold the anterior portion and the posterior portion of the outer circumference of the ring of the inflatable bladder in a deflated state, and wherein the cover is configured to cover the indentation including the inflatable bladder in the deflated state.

7. The medical device of claim 1, wherein when inflated, the inflatable cuff expands radially from the scope channel.

8. The medical device of claim 7, wherein the inflatable cuff is configured when inflated, to create a seal with a wall of the proximal esophagus.

9. The medical device of claim 7, further comprising:

a first inflation lumen coupled to the inflatable bladder; and a second inflation lumen coupled to the inflatable cuff.

10. The medical device of claim 9, further comprising:

a pressure regulator configured to:

adjust a first pressure in the inflatable bladder using the first inflation lumen; and adjust a second pressure in the inflatable cuff using the second inflation lumen.

11. The medical device of claim 1, further comprising:

an outertube forming an interior space that houses at least a portion of the scope channel proximal to the inflatable bladder and distal from a proximal opening of the scope channel, wherein an interior wall of the outertube and an exterior wall of the scope channel form an intraluminal space, wherein the intraluminal space provides a passageway for air flow into the hypopharynx of the patient and into the inner hole of the ring of the inflatable bladder in the trachea of the patient.

12. The medical device of claim 11, further comprising an adapter, wherein the adapter includes:

a first proximal mouth that forms a seal around the proximal opening of the scope channel;

a distal mouth that forms a seal around the outertube;

a second proximal mouth configured for connection to a ventilator or oxygen delivery tubing; and a sealed air flow passageway that extends from the second proximal mouth to the intraluminal space to provide air flow from the second proximal mouth to the intraluminal space.

13. A medical device, comprising:

an airway adapter configured for positioning external to a patient, wherein the airway adapter is configured for connecting to a ventilator or oxygen delivery tubing;

a scope channel coupled to the airway adapter, wherein the scope channel is configured for insertion into a hypopharynx and esophagus of a patient;

an outertube coupled to the airway adapter that encircles the scope channel and extends from a distal end of the airway adapter to at least a middle portion of the scope channel in the hypopharynx of the patient, wherein the outertube has a larger diameter than the scope channel to form an intraluminal space between an interior, anterior wall of the outertube and an exterior, anterior wall of the scope channel, wherein the intraluminal space forms an air passageway, wherein the intraluminal space is configured to allow air to flow from the ventilator or oxygen delivery tubing connected to the airway adapter to the hypopharynx of the patient;

an inflatable bladder attached to an anterior surface of a distal portion of-the scope channel and configured for positioning substantially proximal to the esophagus and distal from the intraluminal space, wherein, in an inflated state, the inflatable bladder forms a ring that extends substantially outwardly at a proximate angle from the anterior surface of the scope channel, wherein the ring forms an inner hole that extends substantially outwardly from the anterior surface of the scope channel, wherein the ring of the inflatable bladder is configured to contact and exert force against an epiglottis in the hypopharynx of the patient and the inner hole of the ring forms an air passageway external to and above the anterior surface of the scope channel, wherein the inner hole is configured to allow the air to flow from the intraluminal space to a trachea of the patient; and an inflatable cuff attached distally from the inflatable bladder on the scope channel and configured for positioning within the esophagus of the patient such that the inflatable cuff and the inflatable bladder are non-overlapping, wherein the scope channel is positioned within an inner hole formed by the inflatable cuff, and wherein when inflated, the inflatable cuff expands radially from the scope channel to provide a seal against an esophageal wall of the patient.

14. The medical device of claim 13, further comprising a bladder base, wherein the bladder base includes:

a posterior surface coupled to the anterior surface of the distal portion of the scope channel;

an anterior surface coupled to a posterior portion of an outer circumference of the inflatable bladder;

an indentation on the anterior surface of the bladder base, wherein the inflatable bladder, in a deflated state, folds into the indentation; and a cover attached by a spring hinge to a distal portion of the anterior surface of the bladder base, wherein the cover extends along a top portion of the indentation and covers the inflatable bladder in the deflated state that is folded into the indentation.

15. The medical device of claim 14, wherein the inflatable bladder, during inflation, exerts a force on a proximal portion of the cover to open the cover; and wherein when the inflatable bladder is inflated, the cover by a recoil action of the spring hinge, returns to a closed position through an inner hole of the inflatable bladder and covers a top portion of the indentation.

* * * * *